United States Patent
Ekins et al.

(10) Patent No.: US 6,564,152 B2
(45) Date of Patent: May 13, 2003

(54) PHARMACOPHORE MODELS FOR, METHODS OF SCREENING FOR, AND IDENTIFICATION OF THE CYTOCHROME P-450 INHIBITORY POTENCY OF NEUROKININ-1 RECEPTOR ANTAGONISTS

(75) Inventors: Sean Ekins, Indianapolis, IN (US); Bill J. Smith, Old Lyme, CT (US)

(73) Assignee: Pfizer Inc, New York, NY (US)

( * ) Notice: Subject to any disclaimer, the term of this patent is extended or adjusted under 35 U.S.C. 154(b) by 120 days.

(21) Appl. No.: 09/765,150

(22) Filed: Jan. 17, 2001

(65) Prior Publication Data

US 2002/0052693 A1 May 2, 2002

Related U.S. Application Data

(60) Provisional application No. 60/178,182, filed on Jan. 26, 2000.

(51) Int. Cl.[7] ............................. G06F 19/00; C12Q 1/00
(52) U.S. Cl. ...................... 702/19; 702/27; 435/4
(58) Field of Search .................... 702/19, 27; 435/4

(56) References Cited

PUBLICATIONS

Ekins et al. Three and four dimensional–quantitative structure activity relationship (3D/4D–QSAR) analyses of CYP2D6 inhibitor Pharmacogenetice, vol. 9, pp. 477–489 (1999).*

Strobl et al. Development of a Pharmacophore for Inhibition of Human Liver Cytochrome P–450 2D6: Molecular Modeling and Inhibition Studies. J. Med. Chem. vol. 36, pp. 1136–1145 (1993).*

Swain et al. Identification of a Series of 3–(Benzyloxy)–1–azabicyclo[2.2.2]octant Human NK–1 Antagonists. J. Med. Chem. vol. 38 pp. 4793–4805 (1995).*

* cited by examiner

Primary Examiner—John S. Brusca
(74) Attorney, Agent, or Firm—Peter C. Richardson; Paul H. Ginsburg; Israel Nissenbaum

(57) ABSTRACT

The present invention relates to novel screening methods which enable the selection of neurokinin-1 (NK-1) receptor antagonist compounds which do not possess significant inhibitory potency towards cytochrome P450 enzymes, in particular, CYP2D6. The present invention also relates to a method of generating a pharmacophore model for the CYP2D6 inhibitory activity of NK-1 receptor antagonist compounds; to methods for the discovery of molecules that are potential NK-1 receptor antagonist compounds which do not possess significant inhibitory potency towards the CYP2D6 enzyme; to methods of modeling the features of the CYP2D6 pharmacophore useful in selecting NK-1 receptor antagonist molecules which do not possess significant potency towards CYP2D6. Further, the invention also relates to pharmaceutical compositions comprising a NK-1 receptor antagonist compound which does not possess significant potency towards the CYP2D6 enzyme identified by methods of the invention; to the uses of a NK-1 receptor antagonist compound identified by the methods of the invention for the manufacture of medicaments and for the treatment of a condition, a disorder or a disease in a mammal for which an NK-1 antagonist receptor compound identified by the method of the invention is therapeutically useful.

15 Claims, 6 Drawing Sheets

PHARMACOPHORE MODELS FOR, METHODS OF SCREENING FOR, AND IDENTIFICATION OF THE CYTOCHROME P-450 INHIBITORY POTENCY OF NEUROKININ-1 RECEPTOR ANTAGONISTS

This application claims the benefit of Provisional application Ser. No. 60/178,182, filed Jan. 26, 2000.

BACKGROUND OF THE INVENTION

The present invention relates to novel screening methods which enable the selection of neurokinin-1 (NK-1) receptor antagonist compounds (e.g., a substance P receptor antagonist) which do not possess significant inhibitory potency towards cytochrome P450 enzymes, in particular, CYP2D6. The present invention also relates to a method of generating a pharmacophore model of NK-1 receptor antagonist compounds which do not possess significant inhibitory potency towards CYP2D6. The invention also relates to methods for the discovery of molecules that are NK-1 receptor antagonist compounds which do not possess significant inhibitory potency towards the CYP2D6 enzyme. The invention also relates to pharmaceutical compositions comprising a NK-1 receptor antagonist compound that does not possess significant inhibitory potency towards CYP2D6 as identified by methods of the invention. The invention further relates to the uses of a NK-1 receptor antagonist compound identified by the methods of the invention for the manufacture of medicaments and for the treatment of a condition, a disorder or a disease in a mammal for which such an NK-1 antagonist receptor compound is therapeutically useful.

In the field of drug development, the developer of pharmaceutical substances must investigate the potential for clinically significant negative drug—drug interactions in the situations where more than one drug may be co-administered to a patient. There is a also significant need in the field of drug development to ascertain the potential existence of these drug—drug interactions prior to commencing any investigation into drug development. The identification of the strong potential usefulness of a chemical compound as early as possible in vitro saves considerable investment of time and resources.

Antagonists for the human NK-1 receptor are likely to be therapeutically useful in treating nausea, asthma, migraine, arthritis, post-operative pain (Takeuchi et al., *J. Med. Chem.*, 41: 3609–3623, 1998) and depression (Kramer et al., *Science*, 281: 1640–1645, 1998). It would therefore be advantageous to be able to ascertain whether or not a useful therapeutic compound will inhibit any drug metabolizing enzymes involved in the clearance of other co-administered pharmaceuticals. There is a critical need for efficient, rapid and reliable methods to select promising candidates in drug discovery that demonstrate potency towards the NK-1 receptor, but not towards drug metabolizing enzymes, such as the cytochrome P450 series.

Drug—drug interactions involving cytochrome P450 enzymes (CYPs) are an important factor in the question of whether a new chemical entity will survive through to the development stage. CYPs are members of a large superfamily of heme-thiolate proteins involved in the metabolism of endobiotics and xenobiotics across eukaryotes and procaryotes. (Nelson et al., *Pharmacogenetics*, 6: 1–42, 1996). The clinical relevance of CYPs are their central role in drug metabolism. They are present in all human tissues and may be inhibited by the co-administration of competing xenobiotics of the same enzyme. (Wrighton et al., *Toxicologic Pathology*, 23: 199–208, 1995). Much less is known about the endogenous functions of CYPs, except for their role in steroid metabolism and recent postulations about their roles in neurotransmitter metabolism (Hiroi et al., *Biochem. Biophys. Res. Commun.*, 249: 838–43, 1998) and signaling pathways (Chan et al., *Proc. Natl. Acad. Sci.*, 95: 10459–10464, 1998). The current understanding of the structural requirements of the CYP active site are presently limited to homology models using $P^{450}{}_{CAM}$, $P^{450}{}_{TERP}$ and $P450_{eryF}$. (Lewis et al., *Xenobiotica*, 27: 319–340, 1997).

One of the human CYPs, CYP2D6, has been well studied. The polymorphic enzyme, CYP2D6, represents only approximately 1.5% of the total human hepatic P450 (Shimada et al., *J. Pharmacol. & Exp. Pharmacol.*, 270: 414–423, 1994), yet participates in the metabolism of over 30% of clinically prescribed drugs (Lewis et al., supra.) including many which have a narrow therapeutic index. (Spatzenegger and Jaeger, *Drug Metabolism Reviews*, 27: 397–417, 1995; Wu et al., *Biochem. Pharmacol.*, 53: 1605–1612, 1997; Lewis et al., supra.). The clinical relevance of CYP2D6 is notable as approximately 7% of Caucasians are poor metabolizers of CYP2D6 substrates while 1% are ultrarapid metabolizers of CYP2D6 substrates. (Brosen, *Ther. Drug Monitoring*, 18: 393–396, 1996). If a drug, which is an inhibitor of CYP2D6, is co-administered with a drug which has CYP2D6-mediated biotransformation as its major clearance mechanism, there is the potential danger of the occurrence of a clinically hazardous event depending on the concentration of the drugs at the enzymes in question.

Therapeutic drug monitoring of CYP2D6 modulators is costly and impacts on health care costs; thus minimizing interactions with CYP2D6 is advantageous to the patient and the entire health care system. Ultimately, knowledge of CYP2D6 inhibitory potential may impact on whether a drug will be co-administered with drugs which are known substrates of CYP2D6. Accordingly, the ability to predict the likelihood of a molecule being a CYP2D6 inhibitor early in the discovery process allows for the more efficient synthesis of suitable candidate molecules without the structural features which cause undesirable inhibition. A means of screening for drugs which do not have significant interaction with the CYP2D6 enzyme is therefore desirable.

Present technologies have centered around the use of in vitro testing using human liver microsomes or recombinant CYPs and a known catalytic probe for CYP2D6 such as bufuralol. However, the possible volume of in vitro studies is often limited by equipment and materials cost, incubation volume and the rate of analytical determination. Alternatives to in vitro techniques as a preliminary screen, enabling the selection of compounds for later study in vitro, would need to be fast, cost effective and reliable.

One such alternative, embraced by the present invention, is the use of computational quantitative structure activity relationship (QSAR) modeling techniques as a screening device for inhibitory potency towards CYP2D6. In the past, computational techniques have led to the production of some computer generated substrate templates, pharmacophores as well as homology models of the active site of CYPs. A pharmacophore model generated by SYBYL has been derived from CYP2D6 inhibitors of bufuralol 1'-hydroxylation as a selective probe for generating $K_i$ values. (Strobl et al., *J. Med. Chem.*, 36:1136–1145, 1993). This inhibitor pharmacophore model suggested that a positive charge on a nitrogen atom and a flat hydrophobic region extending to 7.5 Å virtually perpendicular along the N-H axis are requirements for inhibitory activity. (Strobl et al., Id.). Very recently, attempts at pharmacophore modeling of diverse inhibitors using CATALYST™ have been described which were used prospectively or retrospectively to predict inhibitor binding affinity for CYP2D6 (Ekins et al., *Pharmacogenetics*, 9: 477–489, 1999).

To date, however, closely related molecules from a single therapeutic class have not been used to model the CYP2D6 active site from the point of view of inhibitory activity. There have only been QSAR models from other CYPs generated using a single therapeutic class of compounds, such as quinolones for CYP1A2 (Fuhr et al., *Mol. Pharmacol.*, 43: 191–199, 1993) or warfarin analogs for CYP2C9 (Jones et al., *Drug Metabolism & Disposition*, 24: 1–6, 1996).

Approaches towards modeling the common features of substrates and inhibitors of human CYPs in general from data generated in vitro have been recently shown using a CATALYST™ pharmacophore approach (Ekins et al., supra; Ekins et al., *J. Pharmacol. & Exp. Ther.*, 288: 21–29, 1999; Ekins et al., *J. Pharmacol. & Exp. Ther.*, 290: 429–438, 1999; Ekins et al., *J. Pharmacol. & Exp. Ther.*, 291: 424–433, 1999), comparative molecular field analysis (COMFA) (Jones et al., supra), and a molecular descriptor method (Bravi and Wikel, in press, *Quant. Struct. Act. Rel.*, 2000). Two of these 3D-quantitative structure activity relationship (3D-QSAR) techniques have also been used to predict a test set of molecules absent from the training set (Ekins et al., *J. Pharmacol. & Exp. Ther.*, 288: 21–29 (1999)). The utility of predictive CYP2D6 inhibitor pharmacophores had been recently shown in comparison to $K_{i\ (apparent)}$ data (Ekins et al., *Pharmacogenetics*, 9: 477–489, 1999) where models generated with the CATALYS™ program exhibited reasonable success in the prediction of $K_{i\ (apparent)}$ values for molecules in a test set, outside of the training set.

With respect to NK-1 receptor antagonists, the only pharmacophores for such antagonists had been generated with those same antagonist compounds (Cascieri et al., *Mol. Pharmacol.*, 47: 660–665 (1995); Jacoby et al., *J. Receptor & Signal Transfer*, 17: 855–873 (1997); Takeuchi et al., *J. Med. Chem.*, 41: 3609–3623 (1998)). Site-directed mutagenesis studies have suggested a number of amino acids important for binding NK-1 antagonists (see, Underwood et al., *Chem. Biol.*, 1: 211–221 (1994)). Similarly, structure alignments have suggested likely amino acids important within the receptor for binding molecules with either nitrogens in a quinuclidine ring or piperazine ring, acyclic amino ether, and N-acyl-tryptophan moieties (Cascieri et al., supra). This suggested accommodation of structural diversity may allow the synthesis of NK-1 antagonists without potent CYP2D6 interaction. Most recently a pharmacophore model for 30 non-peptidic and peptidomimetic NK-1 antagonists suggested two main structural fragments, one with at least two off-set stacked aromatic rings and the other with features necessary for hydrophobic, H-bond and salt bridge interactions (Jacoby et al., supra). Molecular structures were also docked in the receptor models to show how water soluble peptidomimetics protrude outside of the binding site. In contrast, a CoMFA model of 72 NK-1 antagonists refuted the stacked conformation of the two aromatic groups as this produced a less predictive model when assessed using a test set of 18 molecules (Takeuchi et al., supra).

The pharmacophore model of the present invention for the CYP2D6 inhibitory activity of NK-1 receptor antagonist compounds makes possible the screening, discovery and selection of molecules that possess the desired activity with respect to the NK-1 receptor without having undesired interaction with the CYP2D6 enzyme.

SUMMARY OF THE INVENTION

The present invention is directed to a method of generating a pharmacophore model for the CYP2D6 inhibitory potency of NK-1 receptor antagonist compounds comprising the steps of (i) generating a set of three-dimensional conformers for each of the compounds in a training set comprising five or more NK-1 receptor antagonist compounds;

(ii) correlating each of the compounds of said training set with an observed value for CYP2D6 inhibitory potency;

(iii) generating from the conformers generated in step (i) a set of one or more pharmacophore test models, each said pharmacophore test model comprising three or more CYP2D6 enzyme active site features selected from the group consisting of the hydrogen bond donor feature, the hydrogen bond acceptor feature, the hydrophobic region feature, the ionizable region feature and the ring aromatic feature, arranged in three-dimensional space;

(iv) calculating the CYP2D6 inhibitory potency for each conformer generated in step (i) towards each of the pharmacophore test models generated in step (iii);

(v) calculating the total cost (or goodness of fit) for each pharmacophore test model; and (vi) choosing the lowest cost (or best fit) pharmacophore test model as the pharmacophore model.

Preferably, each of the steps of the methods of the invention are carried out using molecular modeling software, more preferably one such as CATALYST™ version 4 (Molecular Simulations, Inc., San Diego, Calif.), or other modeling programs known to those of skill in the art.

The term "training set," as used herein, refers to the set of compounds used to build the pharmacophore model that possess known CYP2D6 inhibitory activity. The training set of NK-1 receptor antagonist compounds in step (i) are preferably chosen from known NK-1 antagonist compounds with CYP2D6 inhibitory activity $IC_{50}$ values which span at least three orders of magnitude, more preferably from approximately 0.01 µM to 250µM. One preferred method uses a training set of at least 18 compounds, and most preferably, at least 26 compounds. Another preferred method uses training sets of compounds selected from those listed in Tables I and II. Further, the number of conformers in step (i) is preferably limited to 175 conformers, more preferably 255 conformers, with a potential energy range of 50 Kcal/mole, preferably 35 Kcal/mole, most preferably 10 Kcal/mole.

The term "pharmacophore test model" as used herein, refers to a best guess (whether random or based upon a composite skewed in favor of the compounds in the training set exhibiting a high degree of CYP2D6 inhibitory potency) for the three-dimensional orientation of a set of features which describe the physical, chemical and/or electronic environment of the active site of the CYP2D6 enzyme, said features comprising, e.g., the hydrogen bond donor feature, the hydrogen bond acceptor feature, the hydrophobic region feature, the ionizable region feature and the ring aromatic feature. Preferably, in step (iii), at least ten pharmacophore test models are generated.

In step (iv), the calculation of the CYP2D6 inhibitory potency for each of the conformers of the compounds towards a particular pharmacophore test model is preferably performed via a "fast-fit" algorithm which finds the optimum fit of the particular conformer of a compound to a particular pharmacophore test model without performing an energy minimization on the conformers of the compound. The calculated CYP2D6 inhibitory potency may be calculated by means of a linear regression equation, among other techniques, which correlates the input parameters, i.e., the observed CYP2D6 inhibitory potency of a particular compound, with the features present in that compound. Solving the equation for a particular conformer in a particular pharmacophore test model yields a calculated inhibitory potency value. Preferably the CYP2D6 inhibitory potency is based upon observed $IC_{50}$ values.

The total "cost" (or goodness of fit) for each pharmacophore test model in step (v) is calculated from the deviation between the estimated CYP2D6 inhibitory activity and the observed activity for each compound combined with the number of pharmacophore features in the pharmacophore test model. The pharmacophore test model with the lowest "cost" (or deviation between estimated and observed activity) is the model that is selected as it generally possesses features representative of all of the generated pharmacophore test models. Preferably, the observed CYP2D6 activity is given by the $IC_{50}$ values measured in vitro of the inhibition of recombinant CYP2D6 enzyme activity in the presence of a known substrate, such as in the bufuralol l'hydroxylase assay. However, measured $K_i$ or percent inhibition values may also be used as indicators of observed activity.

The present invention also relates to a method for screening an NK-1 receptor antagonist compound for significant inhibitory potency towards CYP2D6 comprising the steps of (i) finding the optimum fit of the NK-1 antagonist compound to the pharmacophore model of the present invention;

(ii) calculating the CYP2D6 inhibitory potency for the NK-1 antagonist compound.

Another preferred method of the present invention for generating a pharmacophore model for the CYP2D6 inhibitory potency of NK-1 antagonist compounds comprises the step of (i) correlating the chemical features of a training set of NK-1 receptor antagonist compound conformers with a set of two- and/or three-dimensional descriptors for the active site of the CYP2D6 enzyme;

(ii) generating an equation relating the observed CYP2D6 inhibitory potency of the training set of NK-1 antagonist compounds to a set of generated two- and/or three-dimensional descriptors for the NK-1 antagonist compound.

The pharmacophore model in this instance is in the form of an equation. Preferably, each of the steps of the methods of the invention are carried out using molecular modeling software, more preferably one such as CERIUS™ (Molecular Simulations, Inc., San Diego, Calif.), or other modeling programs known to those of skill in the art.

Preferably, the steps of this method may be carried out using the set of two- and/or three-dimensional descriptors for a compound molecule found in the 3D-QSAR functionality of CERIUS$^{2}$™. Step (ii) of the method is preferably carried out using a genetic function approximation (GFA) equation. However, one may also use principle component analysis or partial least squares to correlate descriptors and activity. In addition, there are other regression techniques (linear or non-linear) available and known to those of skill in the art to perform this correlation.

The present invention is also directed to a method for screening NK-1 receptor antagonist compounds for CYP2D6 inhibitory potency comprising the steps of (i) generating the two- and/or three-dimensional descriptors for an NK-1 antagonist compound;

(ii) inputting said two- and/or three-dimensional descriptors into a pharmacophore model equation relating the measured CYP2D6 inhibitory potency of a training set of NK-1 antagonist compounds to a set of two- and/or three-dimensional descriptors generated for those NK-1 antagonist compounds; and (iii) solving said equation for the inhibitory activity of the NK-1 antagonist compound corresponding to the generated three-dimensional descriptors of step (i).

Steps (i) through (iii) are preferably carried out using a software program, e.g., CERIUS$^{2}$™, among others, known to those of skill in the art.

The present invention is also directed to a pharmacophore model for the CYP2D6 inhibitory potency of NK-1 antagonist compounds generated in accordance with the methods of the present invention. The pharmacophore model of the invention is preferably three-dimensional and comprises a set of features, each of which is defined by Cartesian coordinates, x, y and z, which represent the centroid of the feature, and a vector for each feature originating from the centroid of the feature, the direction of which vector is also defined by Cartesian coordinates. The vector represents the optimal directionality of the feature, e.g., the direction of an optimal hydrogen bond for hydrogen-bonding features, inter alia. Preferably, the model comprises at least four features: 1 hydrogen bond donor, 1 hydrophobic feature and 2 ring aromatic features. In another embodiment, the model comprises at least five features: 3 hydrophobic features, 1 positive ionizable feature and 1 ring aromatic feature.

The coordinates of the model of the invention defines the relative relationship between the features, and therefore, those of skill in the art will recognize that the specific coordinates are dependent upon the specific coordinate system used, and thus, although rotation or translation of these coordinates may change the specific values of the x, y and z coordinates, the coordinates will define the claimed model. Those skilled in the art will also recognize that the model of the invention may encompass any model, after optimal superposition of the models, comprising the identified features and having a root mean square of equivalent features of less than about 3.0 Å. More preferably, the model of the invention encompasses any model comprising the identified features and having a root mean square of equivalent features of less than about 1.5 Å, and most preferably, less than about 1.0 Å.

The present invention also relates to a method for identifying NK-1 antagonist compounds, which do not possess significant inhibitor potency towards CYP2D6, from structural and literature databases of experimental compounds comprising the use of the pharmacophore model generated in accordance with the methods of the present invention. In a preferred embodiment, an NK-1 antagonist compound which does not possess significant inhibitory potency towards CYP2D6 is identified by predicting the $IC_{50}$ value of said compound. Preferably, the $IC_{50}$ value for an NK-1 antagonist compound, which does not possess significant inhibitory potency towards CYP2D6, is greater than or equal to 1 µM; more preferably, greater than or equal to 10 µM; and most preferably, greater than or equal to 100 µM.

The present invention also relates to NK-1 antagonist compounds, which do not possess significant inhibitory potency towards CYP2D6, identified by the methods of the present invention. Further, the present invention is directed to pharmaceutical compositions comprising an NK-1 antagonist compound that does not possess significant inhibitory potency towards CYP2D6 identified by the methods of the present invention.

The present invention further relates to methods of treatment for a condition, disorder or disease for which an NK-1 antagonist receptor compound is therapeutically useful comprising the administration of an NK-1 receptor antagonist compound that does not possess significant potency towards CYP2D6, a pharmaceutically acceptable derivative or pharmaceutical composition thereof, identified by a method of the present invention comprising the use of the pharmacophore model of the invention. The condition, disease or disorder may be selected from the group consisting of nausea, asthma, migraine, arthritis, post-operative pain and depression.

The present invention is also related to a method of designing de novo compounds that are NK-1 antagonist compounds which do not possess significant inhibitory potency towards CYP2D6 comprising the step of (i) correlating the two- and/or three-dimensional descriptors for a pharmacophore model for NK-1 antagonist compounds that possess significant inhibitory potency towards CYP2D6 with randomly generated molecules having chemical features corresponding to said descriptors; and (ii) choosing a generated molecule with a CYP2D6 $IC_{50}$ of 1 $\mu$M or greater. Preferably, the CYP2D6 inhibitory activity should correspond to an $IC_{50}$ of 10 $\mu$M or greater; more preferably 100 $\mu$M or greater. The compounds having features corresponding to said descriptors may be randomly generated by any variety of computational methods from a library of known chemical features and conformational preferences of chemical groups and multiple chemical groupings.

The present invention is also related to a method of designing de novo NK-1 antagonist compounds which have selective inhibitory potency towards CYP2D6 comprising the step of
 (i) choosing a target degree of CYP2D6 inhibitory potency;
 (ii) generating a set of two- and/or three-dimensional descriptors for a pharmacophore model for NK-1 antagonist compounds that possess significant inhibitory potency towards CYP2D6 corresponding the inhibitory potency of step (i); and
 (iii) correlating said descriptors of step (ii) with compounds having chemical features corresponding to said descriptors.

The present invention relates to a computer comprising a pharmacophore model for the inhibitory potency towards CYP2D6 of NK-1 antagonist compounds generated in accordance with the methods of the present invention. The present invention relates to a computer comprising a pharmacophore model for the CYP2D6 inhibitory potency of NK-1 antagonist compounds for use in the design or screening of a molecular structure having NK-1 receptor antagonist activity and CYP2D6 inhibitory activity.

The term "significant inhibitory potency" in the context of enzyme inhibition, unless otherwise indicated, refers to the ability of a compound over a characteristic concentration range to interfere with the function of said enzyme, whether permanently or temporarily, so as to deprive said enzyme of the ability to effect or participate in the transformation of chemical and/or biological substances.

The term "treating" refers to, and includes, reversing, alleviating, inhibiting the progress of, or preventing a disease, disorder or condition, or one or more symptoms thereof; and "treatment" and "therapeutically" refer to the act of treating, as defined above.

DETAILED DESCRIPTION OF THE INVENTION

Figure 1:
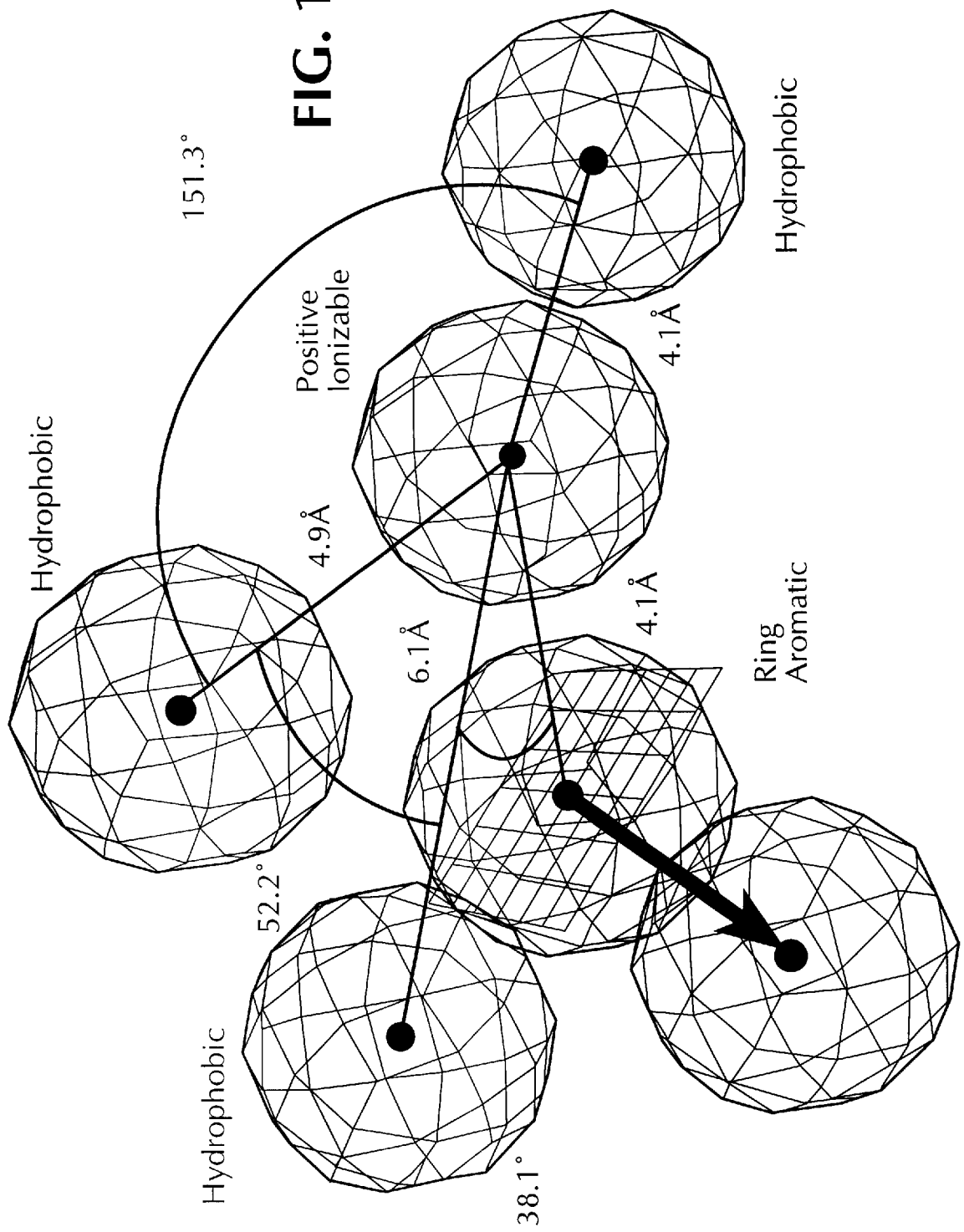
FIG. 1: A CATALYST™ $IC_{50}$ pharmacophore produced from the data in Table I using all 26 molecules illustrating hydrophobic, positive ionizable and ring aromatic features with a vector at right angles to the plane of the ring.

The present invention permits the prediction of the CYP2D6 inhibitory potency of NK-1 receptor antagonist compounds. The methods of the present invention generate various quantitative structure activity relationship (QSAR) models (or pharmacophore models) using in vitro data for the ability of certain non-peptide NK-1 antagonist compounds to inhibit the activity of recombinant CYP2D6. Although in vitro $IC_{50}$ values are more commonly used to assess inhibitory potency, the use of $IC_{50}$ values in the methods of the invention affords the opportunity to build a comprehensive structure activity relationship around an individual CYP.

NK-1 receptor antagonist compounds were used to create training sets for molecular modeling using CATALYST™. This software uses a collection of molecules with inhibitory potency over multiple orders of magnitude for the enzyme of interest, in order to construct a model of the structural features (pharmacophores) necessary for the interaction of molecules with the active site of the enzyme. The resultant pharmacophore test models explain the variability of the potency of inhibition with respect to the geometric localization of these features of molecules.

The computational models constructed by the present invention utilize training sets of NK-1 receptor antagon ists with observed CYP2D6 IC$_{50}$ values varying over three orders of magnitude. The specific compounds utilized in conjunction with the exemplified models are shown in Table I along with observed CYP2D6 IC$_{50}$ values. Nonetheless, the models and methods of the invention are not limited to the use of these particular compounds but encompass the use of other antagonists of the NK-1 receptor known to those of skill in the art.

TABLE I

Structures and CYP2D6 1C$_{50}$ Data for 26 NK-1 Antagonists.

| Compound | Structure | CYP2D6 IC$_{50}$ ($\mu$M) |
|---|---|---|
| I[a] | 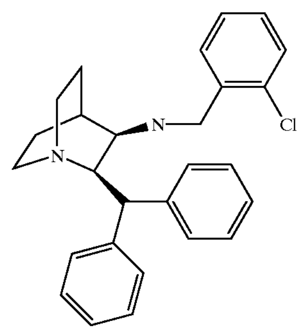 | 0.059 |
| II[b] | 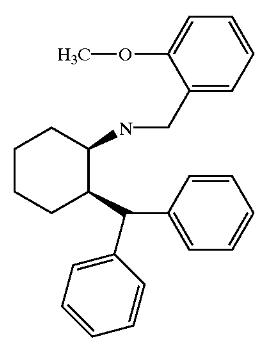 | 0.016 |
| III[c] | 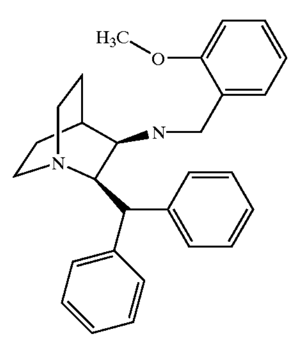 | 0.17 |
| IV[d] | 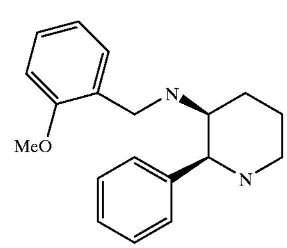 | 0.20 |

TABLE I-continued
Structures and CYP2D6 IC$_{50}$ Data for 26 NK-1 Antagonists.
| Compound | Structure | CYP2D6 IC$_{50}$ ($\mu$M) |
|---|---|---|
| V[e] | 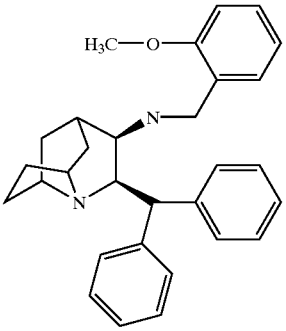 | 0.041 |
| VI[f] | 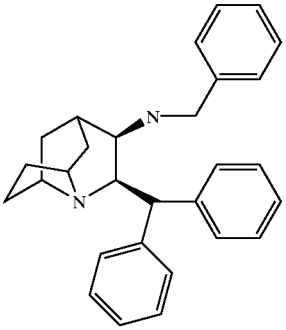 | 0.013 |
| VII[g] | 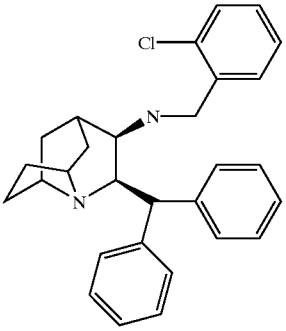 | 0.065 |
| VIII[h] | 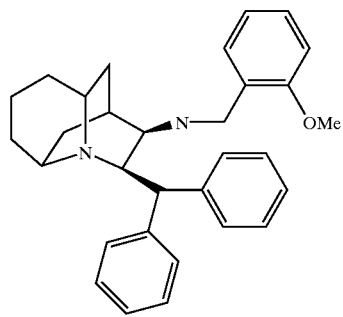 | 0.022 |

TABLE I-continued
Structures and CYP2D6 IC$_{50}$ Data for 26 NK-1 Antagonists.
| Compound | Structure | CYP2D6 IC$_{50}$ ($\mu$M) |
|---|---|---|
| IX[i] | 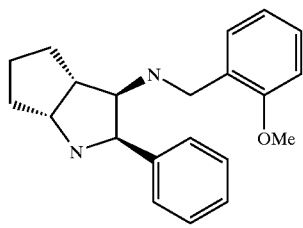 | 0.13 |
| X[j] | 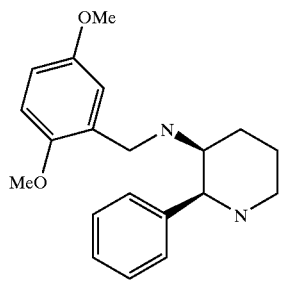 | 0.37 |
| XI[k] | 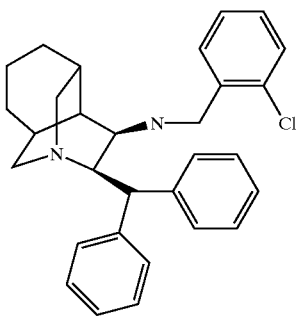 | 0.016 |
| XII[l] | 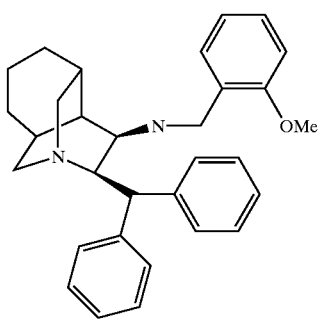 | 0.0067 |

TABLE I-continued
Structures and CYP2D6 IC$_{50}$ Data for 26 NK-1 Antagonists.
| Compound | Structure | CYP2D6 IC$_{50}$ ($\mu$M) |
|---|---|---|
| XIII[m] | 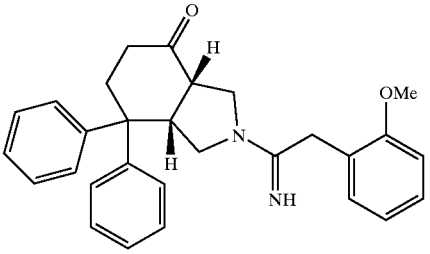 | 0.013 |
| XIV[n] | 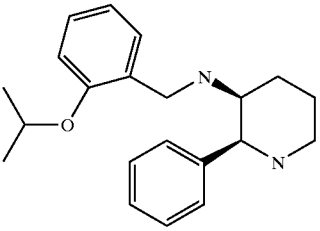 | 0.038 |
| XV[o] | 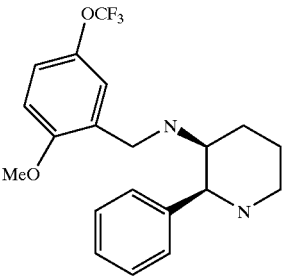 | 0.012 |
| XVI[p] | 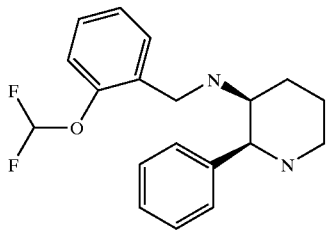 | 0.074 |
| XVII[q] | 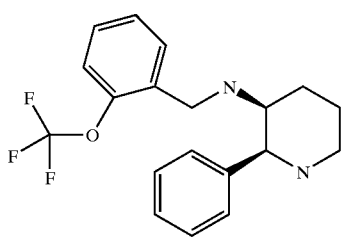 | 0.04 |

TABLE I-continued
Structures and CYP2D6 IC$_{50}$ Data for 26 NK-1 Antagonists.
| Compound | Structure | CYP2D6 IC$_{50}$ ($\mu$M) |
| --- | --- | --- |
| XVIII[r] | 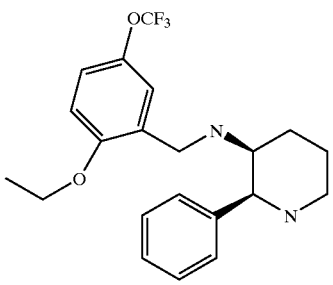 | 0.045 |
| XIX[s] | 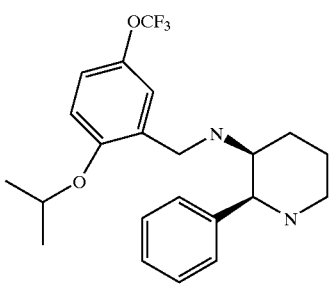 | 0.047 |
| XX[t] | 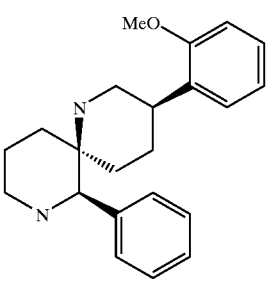 | 0.021 |
| XXI[u] | 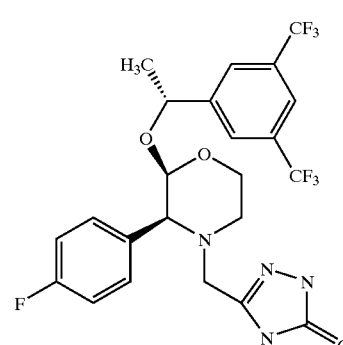 | 18.4 |

TABLE I-continued

Structures and CYP2D6 IC$_{50}$ Data for 26 NK-1 Antagonists.

| Compound | Structure | CYP2D6 IC$_{50}$ ($\mu$M) |
|---|---|---|
| XXII[v] | 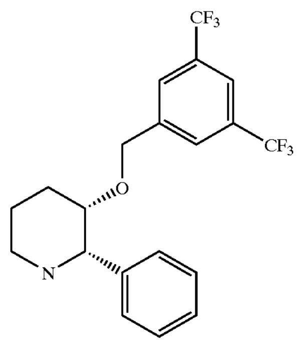 | 0.044 |
| XXIII[w] | 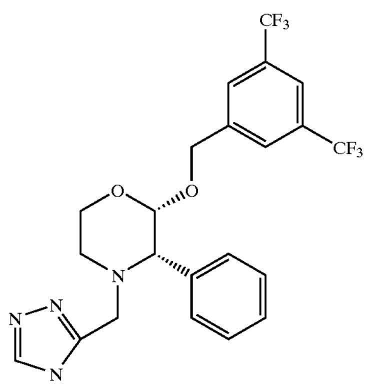 | 8.8 |
| XXIV[x] | 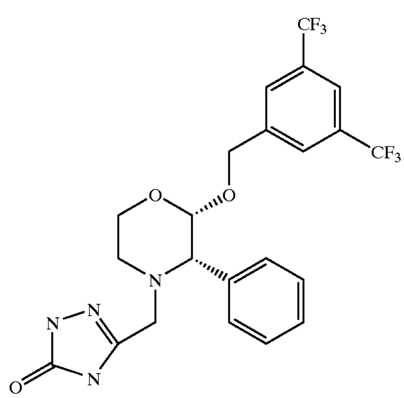 | 7.1 |
| XXV[y] | 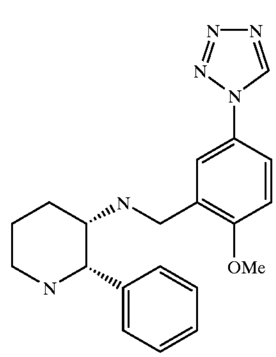 | 0.32 |

TABLE I-continued

Structures and CYP2D6 IC$_{50}$ Data for 26 NK-1 Antagonists.

| Compound | Structure | CYP2D6 IC$_{50}$ ($\mu$M) |
|---|---|---|
| XXVI[z] | (tetrazole-CF$_3$ / OMe / piperidine-phenyl structure) | 0.53 |

[a]Compound 7e, Lowe et al., J. Med. Chem., 35:2591-2600 (1992).
[b]Compound 4, Desai et al., J. Med. Chem., 35:4911-4913 (1992).
[c]Compound 7b, Id.
[d]Compound 3, Desai et al., J. Med. Chem., 35:4911-4913 (1992).
[e]Compound 11a, Lowe et al., J. Med. Chem., 37:2831-2840 (1994a).
[f]Compound 10a, Id.
[g]Compound 12a, Id.
[h]Compound 11b, Id.
[i]Compound 2, Desai et al., Bioorg. Med. Chem. Lett., 4:1865-1868 (1994).
[j]Compound 3e, Rosen et al., Bioorg. Med. Chem. Lett., 8:281-284 (1998).
[k]Compound 24a, Lowe et al., J. Med. Chem., 37:2831-2840 (1994).
[l]Compound 23a, Id.
[m]RP67580, Garret et al., Proc Natl. Acad. Sci., 88:10208-10212 (1991).
[n]Compound 3a, Rosen et al., Bioorg. Med. Chem. Lett., 8:281-284 (1998).
[o]Compound 3f, Id.
[p]Compound 3b, Id.
[q]Compound 3c, Id.
[r]Compound 3j, Id.
[s]Compound 3k, Id.
[t]Compound 3, Desai et al., J. Med. Chem., 37:4263-4266 (1994).
[u]Compound 17 (L-754.030), Hale et al., J. Med. Chem. Lett., 41:4607-4614 (1998).
[v]L-733,060, Ladduwahetty et al., J. Med. Chem. 39:2907-2914 (1996).
[w]Compound 11, Id.
[x]L-742-694, Hale et al., J. Med. Chem., 41:4607-4614 (1998).
[y]GR-203,040, Ward et al., J. Med. Chem., 38:4985–4992 (1995).
[z]GR-205 ,171, Armour et al., Bioorg. Med. Chem. Lett., 6:1015–1020 (1996).

TABLE II

Predictions for Test Set Using the CATALYST ™ and CERIUS$^2$ ™ (n = 18 Models).

| Compound | IC$_{50}$ Observed ($\mu$M) | IC$_{50}$ CATALYST ™ Model Prediction ($\mu$M) | IC$_{50}$ CERIUS$^2$ ™ Model Prediction ($\mu$M) |
|---|---|---|---|
| XI | 0.016 | 0.096 | 0.038 |
| VI | 0.013 | 0.043 | 0.089 |
| IV | 0.021 | 1.10 | 0.14 |
| XIX | 0.047 | 0.079 | 0.11 |
| XIV | 0.038 | 1.40 | 0.045 |
| II | 0.016 | 0.030 | 0.045 |
| XXV | 0.32 | 0.28 | 0.58 |
| XXIV | 7.1 | 2.3 | 21 |

The model of the three dimensional structure activity relationships (3-D-QSAR) of the commom structural features of the CYP2D6 inhibitor compounds is built, as described herein, using the CATALYST ™ program. In addition, QSAR two- and/or three-dimensional descriptor-based models are constructed, also as described herein, with the CERIUS$^2$™ program. As those of skill in the art will readily recognize, chemically different substructures can present certain identical three-dimensional space-filling features, and accordingly, the models of the present invention comprise features which may or may not correspond to actual functional groups in any given NK-1 antagonist molecule.

In connection with the present invention, the inhibitors of the NK-1 receptor that were identified as displaying significant inhibitory potency towards CYP2D6 were used. CATALYST™ models suggest that hydrophobic and ring aromatic features are descriptors of CYP2D6 inhibitory activity. The use of another modeling technique using the CERIUS$^2$™ program, which although less visual than CATALYST™, generates multiple descriptors for molecules and therefore uses more physicochemical parameters. This is important, as such parameters are useful in determining CYP inhibition and selectivity. The two CERIUS$^2$™ models described herein (n=18 and n=26) contain the same descriptors: Jurs-DPSA (difference in atomic charge weighted surface area), Jurs-WNSA-3 (surface weighted charged partial surface areas) and the partition coefficient, A*log(P). The removal of 8 molecules from the 26 molecule training set facilitated the generation of a test set.

The validity of the predictive nature of the models developed using 18 NK-1 receptor antagonists was also evaluated using a test set of similar NK-1 receptor antagonists not present in this training set. These models enable the database screening for CYP2D6 interaction.

The CATALYST™ model for 18 molecules differed from that with 26 molecules, both models as generated below at Example 2. Two CATALYST™ pharmacophore models were generated from multiple conformers of inhibitors (n=18 or n=26) of recombinant CYP2D6-mediated bufuralol 1′-hydroxylation, e.g., as in Example 1, below. The n=18 model consisted of 4 pharmacophoric features and demonstrated a correlation of observed and predicted $IC_{50}$ values (r=0.82). The n=26 model consisted of 5 pharmacophoric features and an improved correlation (r=0.88). The CATALYST™ model for 18 molecules predicted 6 out of the 8 molecules well, including correctly predicting the least active molecule L-742,694, as shown in Table II.

The CATALYST™ pharmacophore model (n=26) generated in accordance with the methods of the invention has the features as set forth in FIG. 1. As depicted, the model comprises a set of features which are arranged in three-dimensional space and describe a chemical property or characteristic attributable to certain arrangements of atoms within molecules, e.g., a hydrogen bond acceptor may be defined as any nitrogen, oxygen or sulfur atom with at least one available (e.g., non-delocalized) lone electron pair; a hydrogen bond donor may be defined by the availability of an electropositive hydrogen atom; a ring aromatic feature may be a hydrophobic, planar feature (e.g., phenyl, etc.). Complete definitions of these individual features have been described elsewhere and will be understood by those of skill in the art. (Greene et al., *J. Chem. Inf & Comp. Sci.,* 34: 1297–1308, 1994). Cartesian coordinates that are displacements in Angstroms along x, y and z axes define the centroid of each feature of the claimed model. Furthermore, each feature, except for the hydrophobic feature, has an optimal directionality defined by a vector, which originates (tail) from the centroid of the feature and ends (head) in the coordinates provided in the model. For example, for the hydrogen bond acceptor, the model contains the optimal direction for the formation of a hydrogen bond between the feature of the model and a chemical group in the active site of CYP2D6; for the aromatic feature, the vector would be perpendicular to the planes of the aromatic ring and defines the rotation of these features for optimal fit into the active site.

One model generated in accordance with the methods of the invention using the CATALYST™ program comprises four features defined by three-dimensional x, y and z coordinates and the vector as defined below in Table III.

TABLE III

Summary of features and positions for CATALYST ™ (n = 18) model.

| Coordinates | HBD | Vector | Hydro-phobic | Ring Aromatic | Vector | Ring Aromatic | Vector |
|---|---|---|---|---|---|---|---|
| X | -2.18 | -3.07 | -0.96 | 2.15 | 1.02 | -0.18 | -1.77 |
| Y | -0.55 | -2.29 | -5.65 | -0.01 | 0.30 | -0.25 | -2.64 |
| Z | 0.05 | -2.25 | 0.25 | -0.34 | -3.16 | 3.80 | 2.92 |

In addition, a further model generated in accordance with the methods of the invention using the CATALYST™ program comprises five features and vectors as set forth in Table IV.

TABLE IV

Summary of features and positions for CATALYST ™ (n = 26) model.

| Coordinates | Hydro-phobic | Hydro-phobic | Hydro-phobic | Positive Ionizable | Ring Aromatic | Vector |
|---|---|---|---|---|---|---|
| X | -0.58 | -1.56 | -5.38 | -1.14 | -1.60 | -2.88 |
| Y | 5.64 | -0.02 | -1.87 | 2.20 | -1.74 | -0.75 |
| Z | -1.88 | 4.86 | 2.23 | 0.47 | 1.46 | -0.75 |

The coordinates of the models set forth in the Tables III to IV above define the relative relationship between the features. The coordinates are dependent upon the particular coordinate system used, and those skilled in the art will recognize that, although rotation and translation of these coordinates may change the specific values of these coordinates, they will in fact define the claimed model. The claimed model is intended to encompass any model, after optimal superposition of the models, comprising the identified features and having a root mean square of equivalent features of less than about 3.0 Å. More preferably, the claimed model encompasses any model comprising the identified features and having a root mean square of equivalent features of less than about 1.5 Å, and most preferably, less than 1.0 Å.

CERIUS²™ pharmacophore models generated for n=18 and n=26, however, were both quite similar in terms of descriptor content, although the 18 molecule training set possessed an improved $r^2$ value. Both 3D-QSAR approaches were then used to predict the 8 molecules in the test set.

The two CERIUS²™ QSAR models were produced after generating 102 two- and/or three-dimensional descriptors from the conformers of CYP2D6 inhibitors previously generated in CATALYST™. Using the genetic function approximation, the best n=26 model produced an $r^2$=0.81 and $q^2$=0.72; the best n=18 model produced an $r^2$=0.836 and $q^2$=0.71. Validation of the n=18 CATALYST™ pharmacophore and the CERIUS²™ QSAR models was performed by predicting the $IC_{50}$ of the 8 molecules left out of this training set. CERIUS²™ predicted 8 out of 8 molecules correctly within the 1 log unit residual cutoff. This model could also discriminate between the two least active molecules and the remaining 6 active molecules.

For n=18, the model generated in accordance with the method of the invention using the CERIUS²™ program comprises the equation:

Activity=6.41884−(0.107351*Jurs-DPSA-3)−(0.184164*Jurs-WNSA-3)−(0.385795*AlogP)

For n=26, the model generated in accordance with the method of the invention using the CERIUS²™ program comprises the equation:

Activity=6.32223−(0.186942*Jurs-WNSA-3)−(0.110243*Jurs-DPSA-3)−(0.344995*AlogP).

The equations set forth above define the relative relationship between the descriptors and the $IC_{50}$ values. Those skilled in the art will recognize that these equations may alter slightly due to the nature of the genetic algorithm. These equations define models of the invention, which are intended further to encompass any other model, after superposition of the models comprising the above-identified equations.

The pharmacophore models of the invention can be used to evaluate the inhibitory potency of a compound towards CYP2D6 and thereby identify those NK-1 receptor antagonist compounds which have potent CYP2D6 interactions or inhibitory activity. The compounds being evaluated may be designed de novo using the models of the invention, or alternatively, be a compound, e.g., chosen from a library of compounds. Using the model of the invention and the methods of identification disclosed herein, one may predict the CYP2D6 inhibitory potency of a compound based upon its fit with the pharmacophore model of the invention. Further, one may even predict the relative degree of CYP2D6 inhibitory potency via the methods of the invention by calculation of the $IC_{50}$ value for a compound.

After identifying a NK-1 antagonist to be evaluated for CYP2D6 inhibitory potency, the three-dimensional structure of the compound is determined. This may already have been done if, e.g., the compound is obtained from a structural database wherein three-dimensional x, y and z coordinates are used to define the compound. Alternatively, the three-dimensional structures of small molecules can be readily determined by methods known to those of skill in the art, including but not limited to, X-ray crystallography, nuclear magnetic resonance spectrometry, etc. The structures obtained from structural databases are usually the structures of compounds alone, uncomplexed with other molecules. If the three-dimensional structure is not known, one may use computer programs, including but not limited to, CATALYST™, to predict the three-dimensional structure of the compound. Three-dimensional conformers are generated from a starting structure using methods well known in the art such as, but not limited to, e.g., the Best or Fast Conformational Analyses (Molecular Simulations, Inc., San Diego, Calif.) with an energy set to a range of 0 to 50 Kcal/mol, preferably 0 to 35 Kcal/mole, and most preferably 0 to 10 Kcal/mole, and the maximum number of conformations set to 100, preferably 175, and most preferably 255. The pharmacophore model may be then compared to evaluated subject compounds, i.e., NK-1 receptor antagonists, using tools to compare the structural features of each, such as, e.g., COMPARE™ within the VIEW HYPOTHESIS™ workbench (Molecular Simulations, Inc., San Diego, Calif.).

The degree of fit of a particular compound structure to the pharmacophore model is calculated by determining, using computer methods, if the compound possesses the chemical features of the model and if the features can adopt the necessary three-dimensional arrangement to fit the model. The modeling program will indicate those features in the model having a fit with the particular compound.

In preferred embodiments, the present invention encompasses compounds which are human NK-1 receptor antagonists which do not possess significant inhibitory potency towards the CYP2D6 enzyme as identified by the above-described methods having a useful selectivity and specificity. Absolute values of receptor activity and potency can vary widely and may be readily determined by those skilled in the art based on the desired application of the antagonist and the situations in which CYP2D6 interactions are critical to the acceptability of the antagonist as an effective therapeutic agent. In general, the NK-1 receptor antagonists have an $IC_{50}$ of less than or equal to 100 nM. More preferably, the $IC_{50}$ value is less than or equal to 10 nM, and most preferably, is less than or equal to 1 nM. In more preferred embodiments, the inhibitory potency of the NK-1 antagonist towards CYP2D6 will be represented by an $IC_{50}$ value of 1 $\mu$M or greater; more preferably 10 $\mu$M or greater; and most preferably 100 $\mu$M or greater.

In another embodiment of the invention, a three-dimensional representation of the pharmacophore for the CYP2D6 inhibitory potency of NK-1 receptor antagonist molecules is created. Specifically, a NK-1 receptor antagonist compound is optimally superimposed on the pharmacophore model using computational methods well known to those of skill in the art as implemented in, e.g., CATALYST™ (Molecular Simulations, Inc., San Diego, Calif.). A superposition of structures and the pharmacophore model is defined as a minimization of the root mean square distances between the centroids of the corresponding features of the molecule and the pharmacophore. A van der Waals surface is then calculated around the superimposed structures using a computer program such as $CERIUS^2$ ™ (Molecular Simulations, Inca, San Diego, Calif.). Not being bound by any theory, the van der Waals surfaces of compounds with low $IC_{50}$ values are thought to approximate the shape of the active site in the CYP2D6 enzyme, since these compounds will have the most complementary fit to that site. As noted above, the active site for CYP2D6 has been studied. (see, Strobl et al., supra). The active site volume of CYP2D6 can be utilized, like the pharmacophore models of the invention, to determine the extent of fit of NK-1 receptor antagonist compounds into the enzyme active site, and thereby the extent of inhibition of the enzyme by those compounds. NK-1 receptor antagonist compounds having a better fit into the active site will most likely be more potent inhibitors of the CYP2D6 enzyme, while compounds that, e.g., have poorer fit to the active site, will be less likely to possess significant inhibitory potency towards the human CYP2D6 enzyme.

Fitting of a compound to the active site volume can be done in a number of different ways using computational methods well known in the art. Visual inspection and manual docking of compounds into the active site volume can be done using such programs as QUANTA (Molecular Simulations, Burlington, Mass., 1992), SYBYL (Molecular Modeling Software, Tripos Associates, Inc., St. Louis, Mo., 1992), AMBER (Weiner et al., *J. Am. Chem. Soc.,* 106: 765–784, 1984), or CHARMM (Brooks et al., *J. Comp. Chem.,* 4: 187–217, 1983). This modeling step may be followed by energy minimization using standard force fields, such as CHARMM or AMBER. Other more specialized modeling programs include GRID (Goodford et al., *J. Med. Chem.,* 28: 849–857, 1985), MCSS (Miranker & Karplus, *Function and Genetics,* 11: 29–34, 1991), AUTODOCK (Goodsell & Olsen, *Proteins: Structure, Function and Genetics,* 8: 195–202, 1990), and DOCK (Kuntz et al., *J. Mol. Biol.,* 161:269–288 (1982)). In addition, inhibitor compounds may be constructed de novo in an empty active site or in an active site including some portions of a known inhibitor using computer programs such as LUDI (Bohm, *J. Comp. Aid. Molec. Design,* 6: 61–78, 1992), LEGEND (Nishibata & Itai, *Tetrahedron,* 47: 8985, 1991), and LeapFrog (Tripos Associates, St. Louis, Mo.).

The NK-1 receptor antagonist compounds, which possess no significant CYP2D6 interactions or inhibitory potency, identified using the pharmacophore model and methods of the invention can be administered to a patient, either alone or in pharmaceutical compositions where they are mixed with a suitable carrier(s) or excipient(s) at doses to treat or ameliorate a variety of diseases, conditions and disorders. A therapeutically effective dose further refers to that amount of the compound sufficient to result in amelioration of the disease, condition or disorder.

The pharmaceutical compositions of the present invention comprise NK-1 receptor antagonist compounds that do not possess significant inhibitory potency towards CYP2D6, said compounds may have chiral centers and therefore exist in different enantiomeric forms. Further, the methods of treatment of the present invention comprise the administration of such compounds having chiral centers. Accordingly, this invention includes methods and pharmaceutical compositions, as described above, wherein the NK-1 receptor antagonists, which do not possess significant inhibitory potency towards CYP2D6, employed are optical isomers, tautomers, stereoisomers or mixtures thereof.

The present invention also relates to pharmaceutical compositions comprising a pharmaceutically acceptable acid addition salt of an NK-1 antagonist identified in accordance with the methods of the present invention. Further, the invention also relates to methods of treatment comprising the administration of such an acid addition salt to a subject in need thereof. The possible acids which are used to prepare a pharmaceutically acceptable acid addition salt of a basic NK-1 antagonists employed in the methods of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

The present invention also relates to pharmaceutical compositions comprising a pharmaceutically acceptable base addition salt of an NK-1 antagonist identified in accordance with the methods of the present invention. Further, the invention also relates to methods of treatment comprising the administration of such a base addition salt to a subject in need thereof. The chemical bases that may be used as reagents to prepare a pharmaceutically acceptable base salt of an NK-1 antagonist identified in accordance with the methods of the invention are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also relates to pharmaceutical compositions and methods of treatment that employ isotopically-labeled compounds that are identical to the NK-1 receptor antagonists generated in accordance with the methods of the present invention, but for the fact that one or more atoms are replaced by an atom having an atomic mass or mass number different from the atomic mass or mass number usually found in nature. Examples of isotopes that can be incorporated into the NK-1 receptor antagonists that are employed in the pharmaceutical compositions and methods of the present invention include isotopes of hydrogen, carbon, nitrogen, oxygen, phosphorous, fluorine and chlorine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively. The NK-1 receptor antagonists employed in the pharmaceutical compositions and methods of the present invention, prodrugs thereof, and pharmaceutically acceptable salts of said compounds or of said prodrugs which contain the aforementioned isotopes and/or other isotopes are within the scope of this invention. Certain isotopically-labeled NK-1 receptor antagonists, for example, those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances.

This invention relates both to methods of treating diseases, conditions or disorders in which the NK-1 receptor antagonist, or the pharmaceutically acceptable salt of another therapeutically active agent, are administered together, as part of the same pharmaceutical composition, as well as to methods in which these two active agents are administered separately as part of an appropriate dose regimen designed to obtain the benefits of the combination therapy. The appropriate dose regimen, the amount of each dose administered, and specific intervals between doses of each active agent will depend upon the subject being treated, and the severity of the disorder or condition. Generally, in carrying out the methods of this invention, the NK-1 receptor antagonist will be administered to an adult human in an amount ranging from about 0.05 to about 1500 mg per day, in single or divided doses, preferably from about 5 to about 200 mg/day, and the other pharmaceutically active agent or pharmaceutically acceptable salt thereof will be administered in an amount sufficient to ameliorate the condition being treated. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The NK-1 receptor antagonists and their pharmaceutically acceptable salts that are employed in the pharmaceutical compositions and methods of this invention are hereinafter also referred to as "therapeutic agents." The therapeutic agents can be administered via either the oral or parenteral route. Compositions containing both an NK-1 receptor antagonist or a pharmaceutically acceptable salt thereof will generally be administered orally or parenterally daily, in single or divided doses, so that the total amount of each active agent administered falls within the above guidelines.

The therapeutic agents may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention, when administered separately (i.e., not in the same pharmaceutical composition) are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

As stated above, the NK-1 antagonist may be formulated in a single pharmaceutical composition or alternatively in individual pharmaceutical compositions for simultaneous, separate or sequential use in accordance with the present invention.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g., conventional tabletting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac acetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethyl cellulose, methylcellulose, polyvinyl-pyrrolidone or gelatin.

Preferred compositions for administration by injection include those comprising an NK-1 antagonist, as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g., Tween 20, 40, 60, 80 or 85) and other sorbitans (e.g., Span 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid, Liposyn, Infonutrol, Lipofundin and Lipiphysan. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., eggs phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Compositions for inhalation or insufflation include solutions and suspensions in pharmaceutically acceptable, aqueous or organic solvents or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing devise may be attached to a face mask, tent or intermittent positive pressure breathing machine. Solution, suspension, or powder compositions may be administered, preferably orally or nasally, from devices which deliver the formulation in an appropriate manner.

Compositions of the present invention may also be presented for administration in the form of transdermal patches using conventional technology. The compositions may also be administered via the buccal cavity using, for example, absorption wafers.

The present invention further provides a process for the preparation of a pharmaceutical composition comprising an NK-1 antagonist, which process comprises bringing the NK-1 antagonist into association with a pharmaceutically acceptable carrier or excipient.

When administered in combination, either as a single or as separate pharmaceutical composition(s), the NK-1 antagonist and another pharmaceutically active agent are presented in a ratio which is consistent with the manifestation of the desired effect. A suitable dosage level for the NK-1 antagonist is about 0.05 to 1500 mg per day, preferably about 5 to 200 mg per day. The compounds may be administered on a regimen of up to 6 times per day, preferably 1 to 4 times per day. Other preferred embodiments include the delivery of the NK-1 antagonist using an oral dosage form or by injection.

It will be appreciated that the amount of an NK-1 antagonist required for use in the treatment or prevention of a condition, disorder or disease will vary not only with the particular compounds or compositions selected but also with the route of administration, the nature of the condition being treated, and the age and condition of the patient, and will ultimately be at the discretion of the patient's physician or pharmacist.

The activity of the NK-1 receptor antagonist compounds of the present invention, as such, is determined by their ability to inhibit the binding of substance P at its receptor sites in CHO-cells which reveal NK-1 receptor or IM-9 cells employing radioactive ligands. The NK-1 or substance P antagonist activity of the antagonist compounds identified by the methods of the invention may be evaluated using the standard assay procedure described by M. A. Cascieri et al., as reported in *J. Immunology,* 133: 3260, 1984. This method essentially involves determining the concentration of the individual compound required to reduce by 50% the amount of radiolabeled substance P ligands at their receptor sites in said isolated cow tissues or IM-9 cells, thereby affording characteristic $IC_{50}$ values for each compound tested. More specifically, inhibition of [$^3$H]SP binding to human IM-9 cells by compounds is determined in assay buffer (50 mM Tris-HCl (ph 7.4), 1 mM $MnCl_2$, 0.02% bovine serum albumin, bacitracin (40 μg/ml) leupeptin (4 μg/ml), chymostatin (2 μg/ml) and phosphoramidon (30 μg/ml). The reaction is initiated by the addition of cells to the assay buffer containing 0.56 nM [$^3$H]SP or $^{125}$I Bolton Hunter labeled SP and various concentrations of compounds (total volume; 0.5 ml) and allowed to incubate for 120 minutes at 4° C. Incubation is terminated by filtration onto GF/B filters (presoaked in 0.1% polyethylenimine for 2 hours). Nonspecific binding is defined as the radioactivity remaining in the presence of 1M SP. The filters are placed into tubes and counted using a liquid scintillation counter.

The activity of the NK-1 receptor antagonist compounds of the present invention, as such, is determined by their ability to inhibit the binding of substance P at its receptor sites in IM-9 cells employing radioactive ligands. The substance P antagonist activity of the herein described compounds is evaluated by using the standard assay procedure described by D. G. Payan et al., as reported in the *J. Immunology,* 133:3260 (1984). This method essentially involves determining the concentration of the individual compound required to reduce by 50% the amount of radiolabeled substance P ligands at their receptor sites in said isolated cow tissues or IM-9 cells, thereby affording characteristic $IC_{50}$ values for each compound tested. More specifically, inhibition of [$^3$H]SP or $^{125}$I Bolton Hunter labeled SP binding to human IM-9 cells by compounds are determined in assay buffer (50 mM Tris-HCl (pH 7.4), 1 mM $MnCl_2$, 0.02% bovine serum albumin, bacitracin (40 μg/ml), leupeptin (4 μg/ml), chymostatin (2 μg/ml) and phosphoramidon (30 μg/ml)). The reaction is initiated by the addition of cells to assay buffer containing 0.56 nM [$^3$H]SP and various concentrations of compounds (total volume; 0.5 ml) and allowed to incubate for 120 min at 4° C. Incubation is terminated by filtration onto GF/B filters (presoaked in 0.1% polyethylenamine for 2 hours). Nonspecific binding is defined as the radioactivity remaining in the presence of 1 μM SP. The filters are placed into tubes and counted using liquid scintillation counter.

The adverse effect on $Ca^{2+}$ channel binding affinity of the NK-1 receptor antagonist compounds of the present invention is determined by verapamil binding study in rat heart membrane preparation. More specifically, verapamil binding study is performed as previously described by Reynolds et al., (*J. Pharmacol. Exp. Ther.,* 237:731 (1986)). Briefly, incubations are initiated by the addition of tissue to tubes containing 0.25 nM [$^3$H]desmethoxyverapamil and various concentrations of compounds (total volume; 1 ml). Nonspecific binding is defined as radioligand binding remaining in the presence of 3–10 μM methoxyveraparnil.

The activity of NK-1 receptor antagonist compounds of this invention against generalized anxiety disorder is determined by inhibition of GR73632-induced tapping test in gerbils. More specifically, gerbils are lightly anesthetized with ether and the skull surface is exposed. GR73632 or vehicle (PBS, 5 μl) are administered directly into the lateral ventricles via a 25 gauge needle inserted 4.5 nun below bregma (preceded by pretreatment with an antagonist, 0.1–32.0 mg/kg, s.c. or p.o.). Following injection, gerbils are placed in 1 L beaker individually and monitored for repetitive hind paw tapping.

Compounds and salts can be evaluated as antimigraine agents by testing the extent to which they mimic sumatriptan in contracting the dog isolated saphenous vein strip (P. P. A. Humphrey et al., *Br. J. Pharmacol.,* 94: 1128, 1988). This effect can be blocked by methiothepin, a known serotonin antagonist. Sumatriptan is known to be useful in the treatment of migraine and produces a selective increase in carotid vascular resistance in the anaesthetized dog. It has been suggested that this is the basis of its efficacy by Fenwick et al., *Br. J. Pharmacol,* 96: 83, 1989.

EXAMPLES

Example 1

Bufuralol 1'-hydroxylase Assay (CYP2D6) $IC_{50}$ Determinations

Using a bufuralol-hydroxylation as a marker for CYP2D6 catalytic activity, the inhibitory effect of various NK-1 antagonists were assessed in vitro. The inhibitor compounds of Table I were assayed for CYP2D6 activity by the following procedure.

Two separate plates were prepared for the substrate and for dilutions of inhibitor. The contents of the two plates were combined in a 1:1 ratio to make a master plate of substrate and inhibitor solutions (S/I plate). The remaining assay ingredients, a combination of CYP2D6 (0.1 mg/ml, 0.12 pmol/ml, Panvera, Madison Wis.), NADPH (1.2 mM) and buffer (100 mM sodium phosphate, pH 7.4), are prepared on ice and transferred to a polyvinyl reaction plate (RXN plate). Preparation of these plates require the use of a Soken 96-well pipettor (Apricot Designs Inc., Encino, Calif.) and a Robbins 96-well pipettor. The RXN plate is pre-warmed to 37° C. using a MJ Research Model PTC-100 automated thermal controller, and the reaction is initiated by addition of an aliquot from the S/I plate. The reaction is allowed to proceed at 37° C. before being terminated using 70% perchloric acid (50 µl). HPLC analysis is preceded by filtration of (150µl) using a Millipore multiscreen-MAHA mixed cellulose esters, triton free, non-sterile plate (Millipore Co., Bedford, Mass.). Recombinant CYP2D6 (0.1 mg/ml), bufuralol (3.4 µM), inhibitor (at six concentrations between 0.1 and 10µM) and sodium phosphate (100 MM, pH 7.4) in a total volume of 500 µl were preincubated for 10 minutes at 37° C. before addition of NADPH (Sigma Chemical Co., St. Louis, Mo., 1 mg/ml) and incubation for a further 10 minutes.

The reactions were then terminated as described above and Multiscreen plates were then used to filter the samples by slowly drawing them through the filter plate by a weak vacuum and collecting them in a polypropylene 96-well plate. The plate was mixed by drawing up and expelling well contents twice with the Soken pipettor. A 20 µl volume of each sample was injected for HPLC analysis every 2.5 minutes. When required, concentrations of the inhibitor were adjusted in a repeat experiment to cover concentration ranges above and below the reported $IC_{50}$ value.

The HPLC method was a modification of the procedure of Kronbach et al. *Analytical Biochem.*, 162: 24–32, 1987. The mobile phase consisted of acetonitrile and water 20/80 v/v containing triethylamine (1 ml/liter) and phosphoric acid (600 l/liter) at a flow rate of 0.5 ml/min (analytical side) and 1.8 ml/min (wash side) using a column switching format. HPLC analysis was performed with two alternating HPLC columns (column A and column B) attached to a Valco E36 valve. Between 0 and 5.2 minutes of the run time, column A analyses metabolite peak of sample #1. Between 5.2 and 10.4 minutes of the run time, the flow is diverted to column B for analysis of sample #2, and column A goes through a wash cycle to elute the parent compound. During the wash cycle, the flow to column A is increased to 1.8 ml/min. At 10.4 minutes of the run time, the 0.5 ml/min flow is returned to column A for analysis of sample #3, and column B goes through a wash cycle. The HPLC system utilized a Gilson 233XL injector and dilutor (Gilson, Middleton, Wis.), Jasco pumps (Easton, Md.) and FP-920 fluorescence detector at 252 nm excitation and 302 nm emission. A Phenomex primesphere C1 8-MC, 5 µm, 30×2 mm column (Phenomenex, Torrance, Calif.) was used. The retention time of the 1'-hydroxybufuralol (carbinol) metabolite was 1.0 minute. The peak area of the carbinol metabolite was determined in the absence of inhibitor and compared to that measured in the presence of inhibitor. The percent of control values versus inhibitor concentration were fitted to a Hill equation using non-linear curve fitting methods, namely, Deltagraph (DeltaPoint, Inc., Monterey, Calif.). The inhibitor concentration which reduced the carbinol formation by 50% was defined as the $IC_{50}$. The $IC_{50}$ values measure by the foregoing procedure for 26 NK-1 antagonist compounds are listed in Table I.

Example 2

Molecular Modeling with CATALYST™

Computational molecular modeling studies were carried out using a Silicon Graphics Octane workstation and based on a methodology previously described for CYP2D6 and other CYPs (Ekins et al., *Pharmacogenetics*, 9: 477–489, 1999; Ekins et al, *J. Pharmacol. & Exp. Ther.*, 288: 21–29, 1999; Ekins et al., *J. Pharmacol. & Exp. Ther.*, 290: 429–438, 1999; Ekins et al., *J. Pharmacol. & Exp. Ther.*, 291: 424–433, 1999). The three-dimensional structures of CYP2D6 inhibitors were built interactively using CATALYST™ version 4.0 (Molecular Simulations, San Diego, Calif.).

Two training sets were used for model construction. One consisted of 18 NK-1 compounds (Compounds I, III, V, VII–X, XII, XIII, XV–XVIII, XX–XXIII and XXVI in Table I) and the other contained a further 8 NK-1 compounds (Compounds II, IV, VI, XI, XIV, XIX, XXIV and XXV in Table I). The number of conformers generated for each inhibitor was limited to a maximum of 255 with an energy range of 20 Kcal/mol. Ten hypotheses (or pharmacophore test models) were generated using these conformers for each of the molecules and $IC_{50}$ values generated after selection of the following features for the inhibitors: hydrogen bond donor, hydrogen bond acceptor, hydrophobic and ring aromatic. After assessing all 10 hypotheses (pharmacophore test models) generated for each data set, the lowest cost hypothesis (best fit pharmacophore model) was considered the best.

The goodness of the structure activity correlation was estimated by means of the regression value (r). CATALYST™ also calculated the total cost (goodness of fit) of the generated pharmacophores from the deviation between the estimated activity and the observed activity, combined with the complexity of the pharmacophore test model or hypothesis (i.e., the number of pharmacophore features). A null hypothesis (null test model) is additionally calculated which presumes that there is no relationship in the data and that experimental activities are normally distributed about their mean. Hence the greater the difference between the cost (goodness of fit) of the generated hypothesis (pharmacophore test model) and the cost of the null hypothesis (null test model), the less likely it is that the test model reflects a chance correlation. This criteria was then used as an assessment of the pharmacophore model selected.

Figure 2:
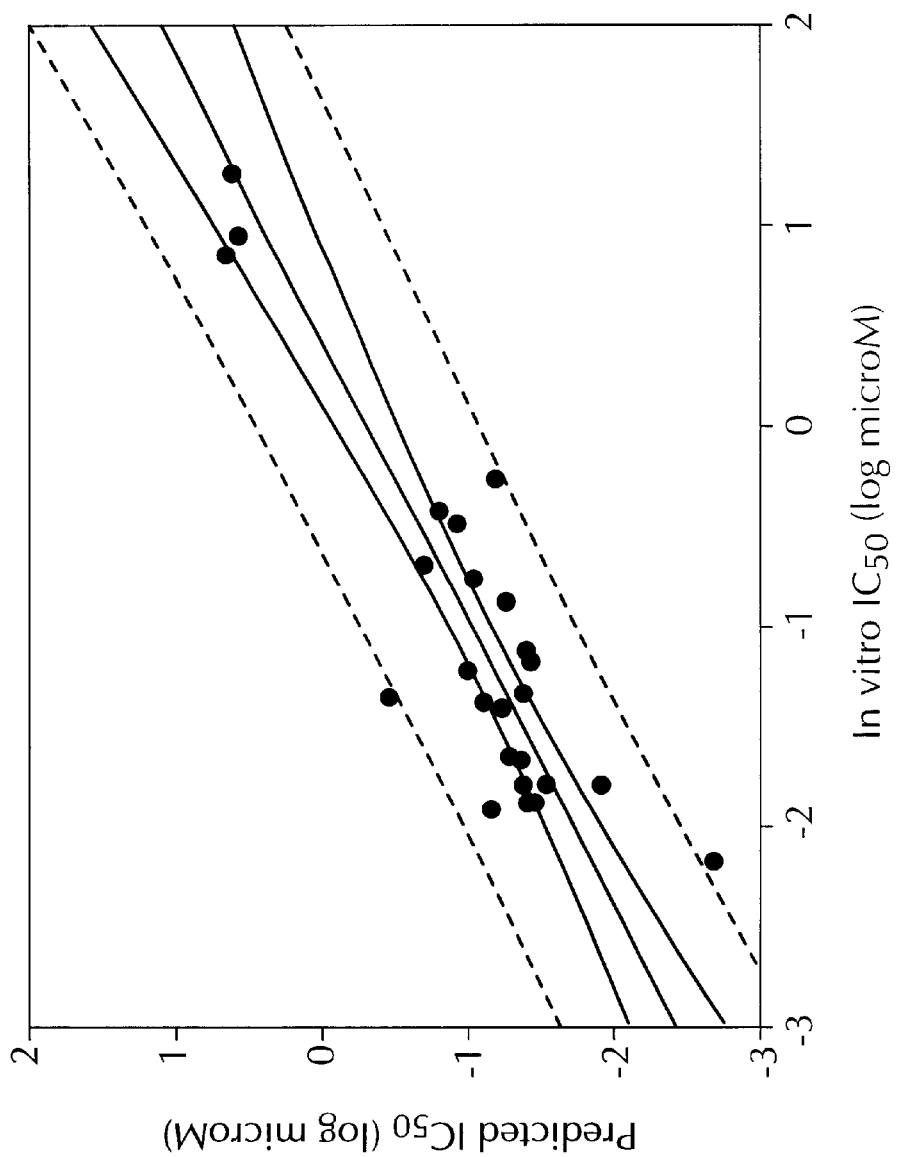
FIG. 2: Linear regression for estimated and observed in vitro activities for the CATALYST™ pharmacophore obtained from 26 CYP2D6 inhibitors. The central line corresponds to the regression for the data, the inner lines represent the 95% confidence interval for the regression while the outer dashed lines are the 95% confidence interval for the population/prediction.
Figure 3:
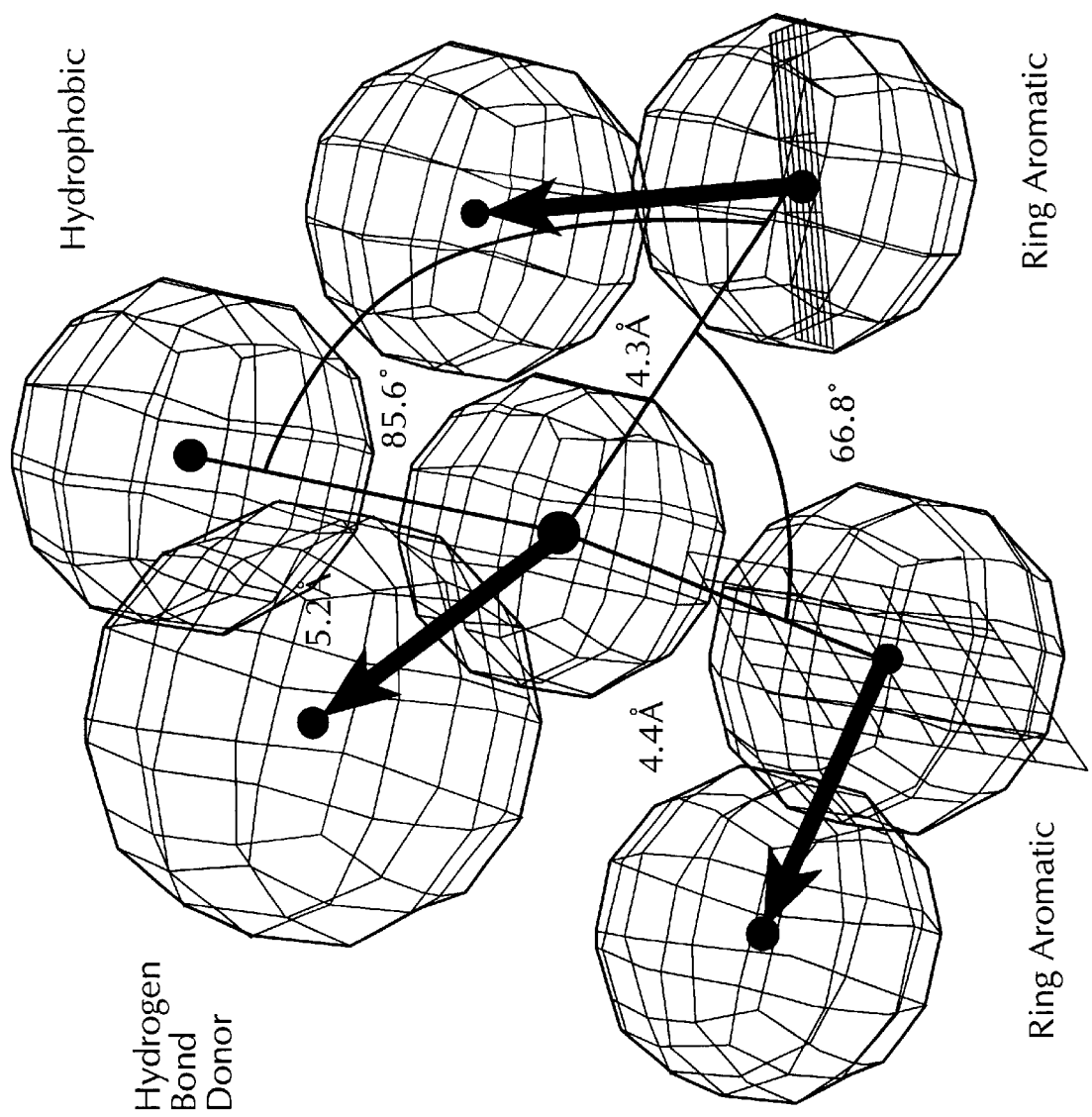
FIG. 3: A CATALYST™ $IC_{50}$ pharmacophore produced from the data using 18 molecules (Compounds I, III, V, VII–X, XII, XIII, XV–XVIII, XX–XXIII and XXVI in Table I) illustrating hydrophobic, hydrogen bond donor and ring aromatic features with a vector at right angles to the plane of the ring.
Figure 4:
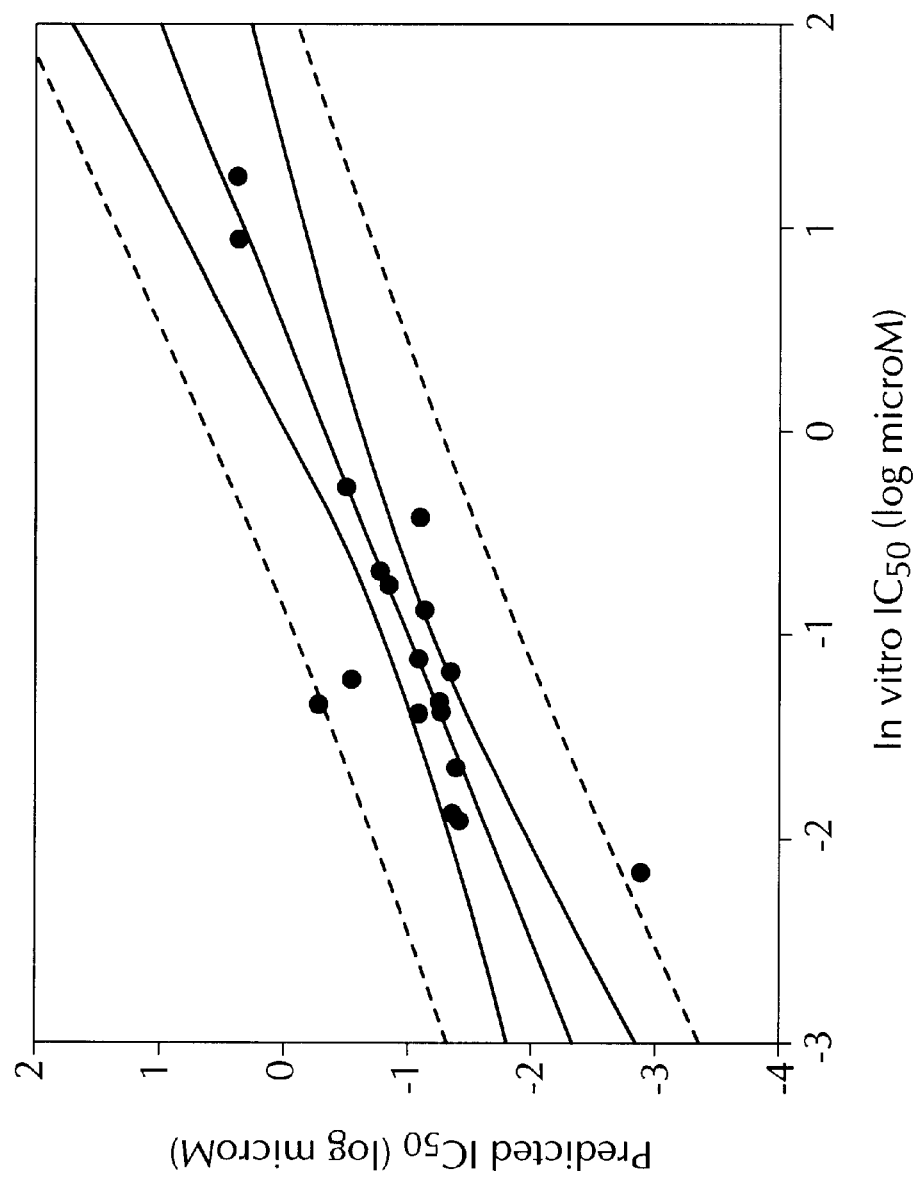
FIG. 4: Linear regression for estimated and observed in vitro activities for the CATALYST™ pharmacophore obtained from 18 CYP2D6 inhibitors (Compounds I, III, V, VII–X, XII, XIII, XV–XVIII, XX–XXIII and XXVI in Table I). The central line corresponds to the regression for the data, the inner lines represent the 95% confidence interval for the regression while the outer dashed lines are the 95% confidence interval for the population/prediction.

Using the training set consisting of 26 molecules, the resulting lowest cost pharmacophore yielded 5 features (FIG. 1) necessary for inhibition of CYP2D6. The pharmacophore consisted of 3 hydrophobic regions, 1 positive ionizable and 1 ring aromatic features. This pharmacophore yielded an excellent correlation of observed versus estimated $IC_{50}$ values (r=0.88, FIG. 2). The total cost of this hypothesis (test model) was 116 compared with the null hypothesis (test model) of 133. When the training set was limited to 18 molecules, the number of features in the optimal model decreased to 4, namely, 1 hydrogen bond donor and 1 hydrophobe and 2 ring aromatic features (FIG. 3). The correlation of observed versus estimated $IC_{50}$ values, the r value, also decreased to 0.82 (FIG. 4). The total cost of this hypothesis (test model) was 88 compared with the null hypothesis (test model) of 9 1.

Example 3

CATALYST™ CYP2D6 Pharmacophore Validation Using a Test Set of $IC_{50}$ Values The iterative improvement of the n=18 model was tested by predicting the 8 molecules left out of the model for the CATALYST™ technique. A test set of 8 compounds (Compounds II, IV, VI, XI, XIV, XIX, XXIV and XXV in Table II) was subjected to the fast-fit algorithm for the CATALYST™ hypothesis (pharmacophore test model) in order to predict an $IC_{50}$ value for each. Fast fit refers to the method of finding the optimum fit of the inhibitor to the hypothesis (pharmacophore test model) among all the conformers of the molecule without performing an energy minimization on the conformers of the molecule. (CATALYST™ tutorials release 3.0, Molecular Simulations, Inc., San Diego, Calif.) These predictions were compared to in vitro values as measured in Example 1. The CATALYST™ model produced 2 false negatives with $IC_{50}$ values greater than 1 µM and these predictions were outside the 1 log unit residual cutoff.

Example 4

Modeling with CERIUS² ™

The n—26 training set molecules were aligned in CATALYST™ on the best hypothesis (pharmacophore test model) then imported into CERIUS² ™. Default two- and three-dimensional descriptors were generated in the 3D-QSAR functionality. Activity values were log transformed and added to the study table. More three-dimensional descriptors were selected including HOMO, LUMO, Jurs and Shadow indices to increase the total number to 102. An equation was generated using the genetic function approximation (GFA) to select descriptors, which related to the CYP2D6 log inhibitory activity. The above process was repeated after removal of the 8 molecules previously described to give the n=18 training set.

The iterative improvement of the n=18 model was tested by predicting the 8 molecules left out of the model for the CERIUS™ technique. The CERIUS™ model correctly predicted all 8 molecules within the residual cutoff and also correctly identified the least potent CYP2D6 inhibitor, Compound XXIV (Table II).

Example 5

CERIUS²™ Model Validation Using a Test Set of IC$_{50}$ Values

The descriptors found to explain activity were generated for the test set of 8 compounds in order to predict an IC$_{50}$ value using the equation produced in CERIUS²™. These predictions were compared with the in vitro observed values to determine how predictive the CERIUS²™ model was using a 1 log unit cutoff and accepting that IC$_{50}$ values less than 1 μM likely represent active compounds in terms of CYP2D6 inhibition.

Figure 5:
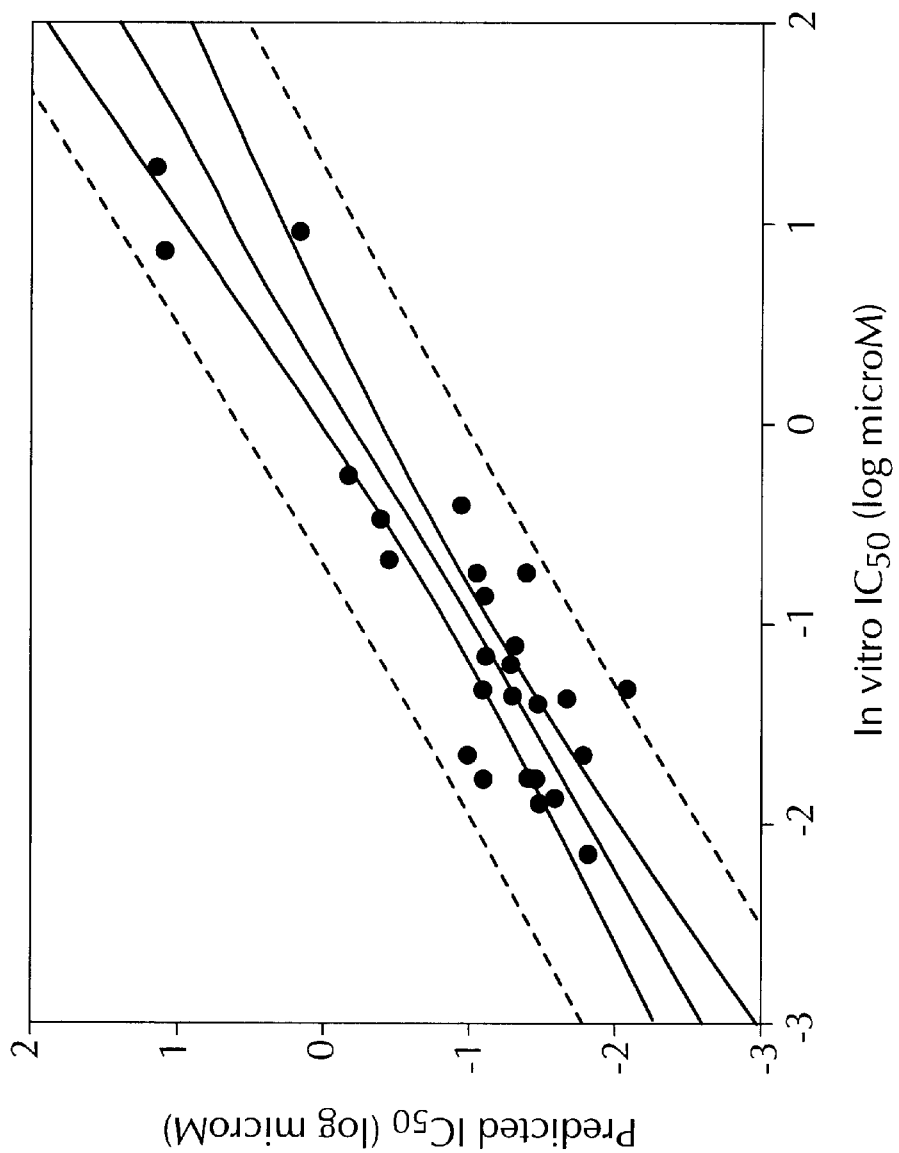
FIG. 5: Linear regression for estimated and observed in vitro activities for the best CERIUS$^2$™ QSAR obtained from 26 CYP2D6 inhibitors. The central line corresponds to the regression for the data, the inner lines represent the 95% confidence interval for the regression while the outer dashed lines are the 95% confidence interval for the population/prediction.
Figure 6:
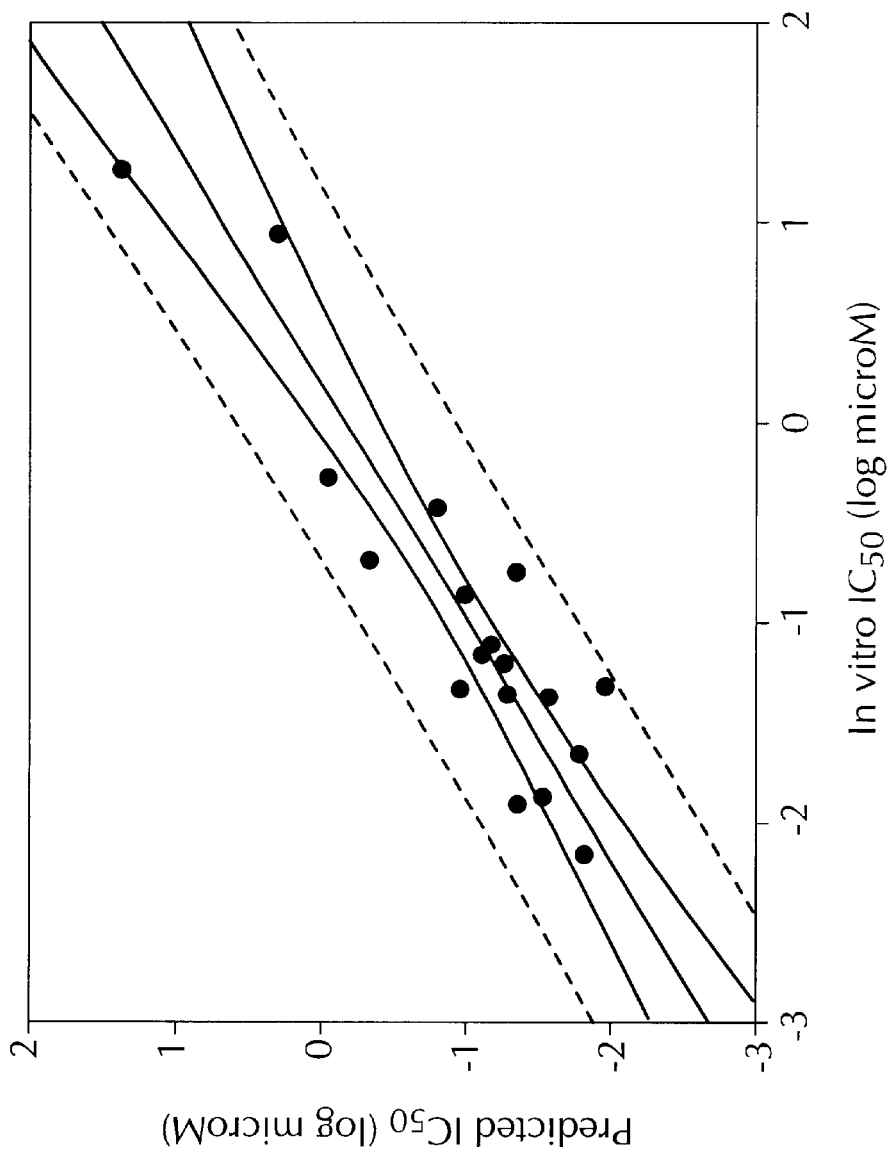
FIG. 6: Linear regression for estimated and observed in vitro activities for the best CERIUS$^2$™ QSAR obtained from 18 CYP2D6 inhibitors (Compounds I, III, V, VII–X, XII, XIII, XV–XVIII, XX–XXIII and XXVI in Table I). The central line corresponds to the regression for the data, the inner lines represent the 95% confidence interval for the regression while the outer dashed lines are the 95% confidence interval for the population/prediction.

The sets of NK-1 antagonists were used to create training sets for 3D-QSAR models using CERIUS²™ Using the 102 descriptors for all 26 molecules and the GFA method enabled selection of the best equation which described the CYP2D6 inhibition. The $r^2$ was 0.81 and the $q^2$ was 0.72 for the initial model (FIG. 5) were "Activity=6.32223−(0.186942*Jurs-WNSA-3)−(0.110243*Jurs-DPSA-3)−(0.344995*AlogP)." Removing the eight molecules from the training set generated with the 102 descriptors resulted in an improved $r^2$=0.836 (FIG. 6) and $q^2$=0.711 for the model described by "Activity=6.41884−(0.107351 *Jurs-DPSA-3)−(0.184164*Jurs-WNSA-3)−(0.385795*AlogP)."

The present invention is not to be limited in scope by the specific embodiments disclosed in the examples which are intended as illustrations of a few aspects of the invention and any embodiments which are functionally equivalent are within the scope of this invention. Further, various modifications of the invention in addition to those shown and described herein will become apparent to those skilled in the art and are intended to fall within the scope of the claims below.

What is claimed is:

1. A method of generating a pharmacophore model for the CYP2D6 inhibitory potency of NK-1 receptor antagonist compounds comprising the steps of
   (i) generating a set of three-dimensional conformers for each of the compounds in a training set comprising five or more NK-1 antagonists;
   (ii) correlating each of the compounds of said training set with an observed value for CYP2D6 inhibitory potency;
   (iii) generating from the conformers of step (i) a set of one or more pharmacophore test models, each said pharmacophore test model comprising three or more of the CYP2D6 enzyme active site features selected from the group consisting of the hydrogen bond donor feature, the hydrogen bond acceptor feature, the hydrophobic region feature, the ionizable region feature and the ring aromatic feature, arranged in three-dimensional space;
   (iv) calculating the CYP2D6 inhibitory potency for each conformer generated in step (i) towards each of the pharmacophore test models generated in step (iii);
   (v) calculating the total cost for each pharmacophore test model; and
   (vi) choosing the lowest cost pharmacophore test model as the pharmacophore model.

2. The method of claim 1 wherein the steps are carried out using a molecular modeling software.

3. The method of claim 1 wherein the steps are carried out with a molecular modeling software program.

4. The method of claim 1 wherein the training set of NK-1 receptor antagonist compounds are chosen from NK-1 receptor antagonist compounds with observed CYP2D6 IC$_{50}$ values spanning at least three orders of magnitude.

5. The method of claim 4 wherein the observed CYP2D6 IC$_{50}$ values vary from 0.01 μM to 250 μM.

6. The method of claim 1 wherein the number of conformers in step (i) is limited to 255 conformers.

7. The method of claim 1 wherein the energy range of the conformers in step (i) is 50 Kcal/mole.

8. The method of claim 1 wherein the energy range of the conformers in step (i) is 35 Kcal/mole.

9. The method of claim 1 wherein the energy range of the conformers in step (i) is 10 Kcal/mole.

10. The method of claim 1 wherein the training set of step (i) contains at least 10 compounds.

11. The method of claim 1 wherein the training set of step (i) contains at least 18 compounds.

12. The method of claim 1 wherein the training set of step (i) contains one or more compounds selected from the group consisting of:

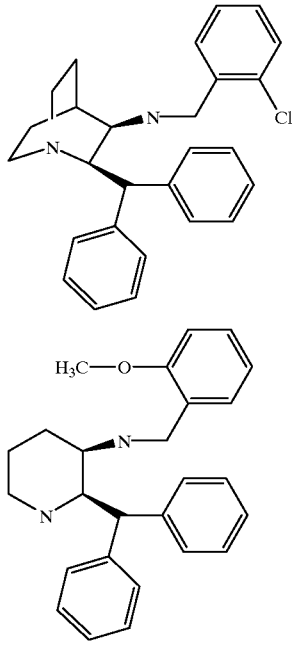

-continued
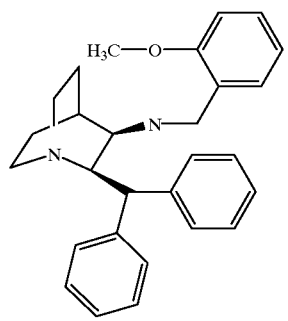
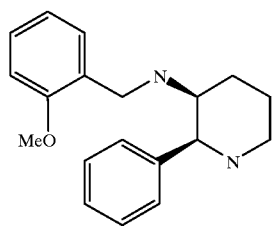
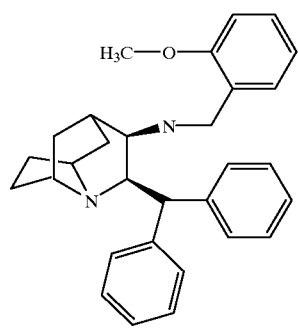
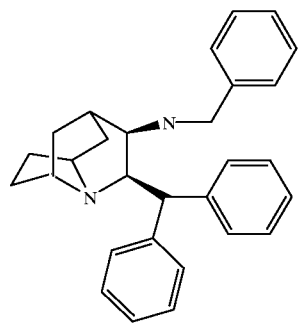
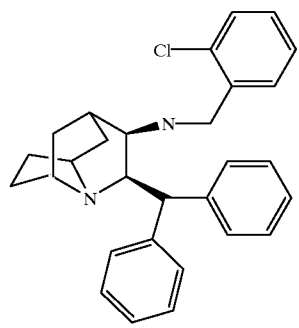
-continued
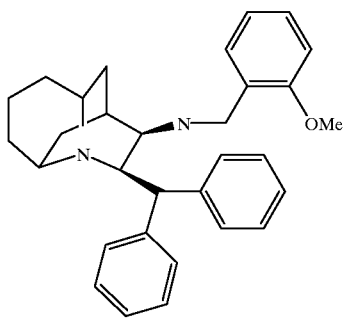
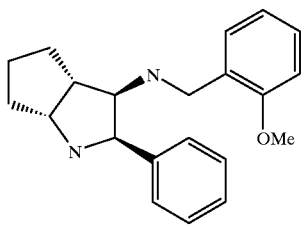
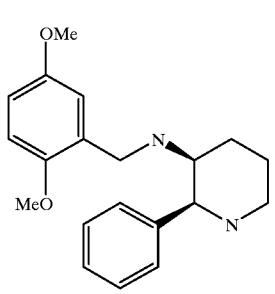
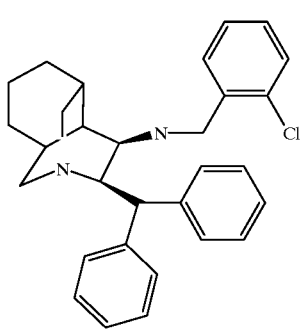
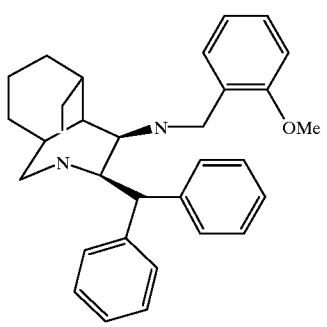

-continued
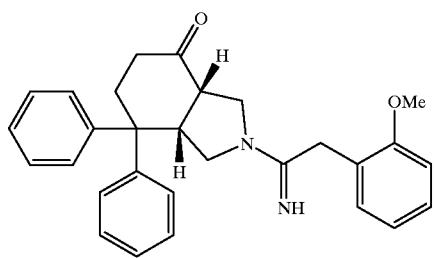
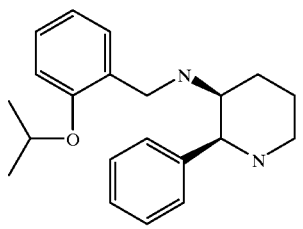
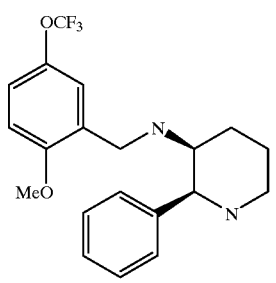
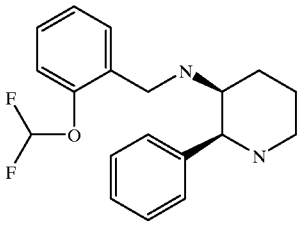
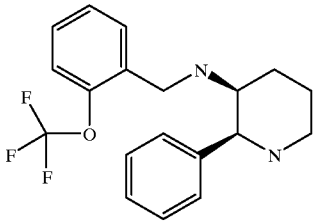
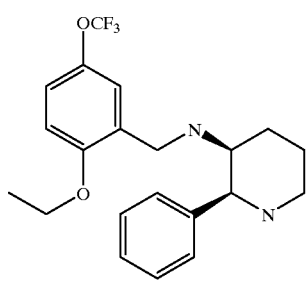
-continued
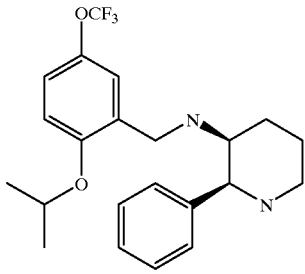
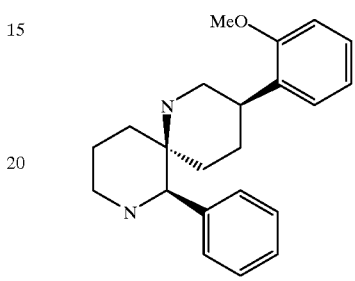
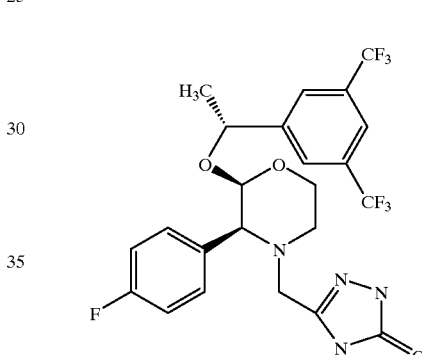
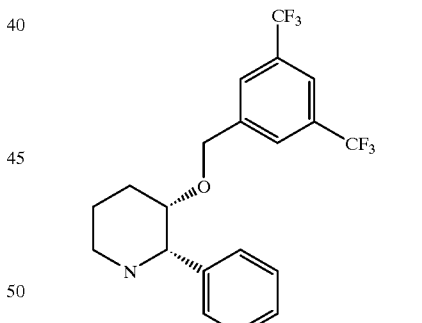
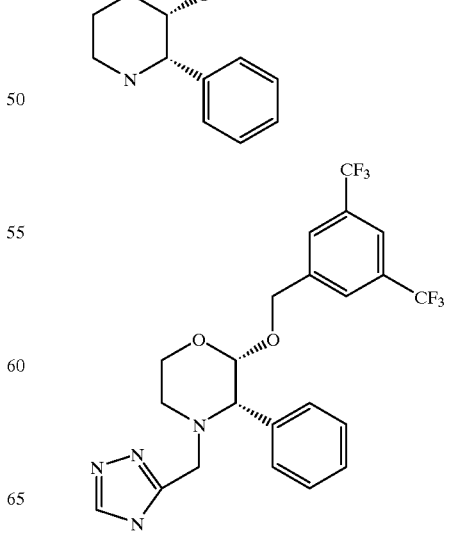

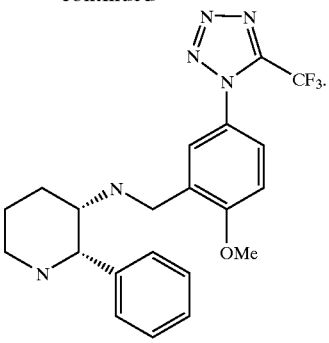
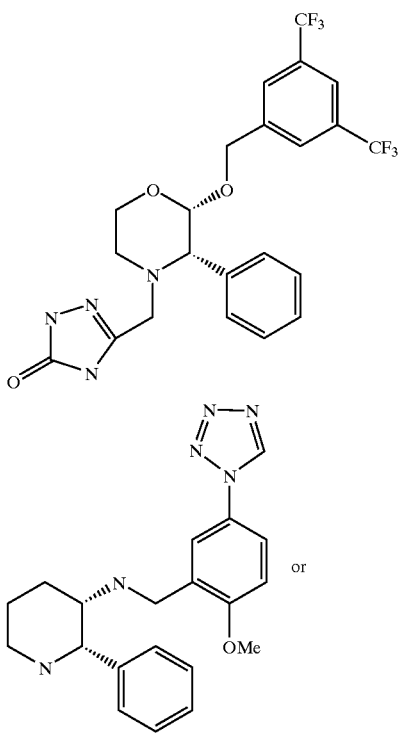

13. The method of claim 1 wherein at least 10 pharmacophore test models are generated in step (ii).

14. A method for screening an NK-1 receptor antagonist compound for CYP2D6 inhibitory potency comprising the steps of:
 (i) finding the optimum fit of the NK-1 antagonist compound to the pharmacophore model of claim 1; and
 (ii) calculating a CYP2D6 inhibitory potency value for the NK-1 antagonist compound.

15. The method of claim 14 wherein finding the optimum fit in step (i) is carried out via the use of a fast-fit algorithm, a principle component analysis, a partial least squares technique, a linear regression technique or a non-linear regression technique.

* * * * *